(12) United States Patent
Garigapati et al.

(10) Patent No.: US 12,338,330 B2
(45) Date of Patent: Jun. 24, 2025

(54) ALGINATE HYDROGEL COMPOSITIONS

(71) Applicant: Takeda Pharmaceutical Company Limited, Osaka (JP)

(72) Inventors: Venkata R. Garigapati, Southborough, MA (US); Tetsuo Hoshino, Arlington, MA (US); Amit Garle, Lowell, MA (US)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 18/310,607

(22) Filed: May 2, 2023

(65) Prior Publication Data

US 2023/0348675 A1 Nov. 2, 2023

Related U.S. Application Data

(62) Division of application No. 16/086,405, filed as application No. PCT/US2017/023371 on Mar. 21, 2017, now Pat. No. 11,655,343.

(60) Provisional application No. 62/312,998, filed on Mar. 24, 2016.

(51) Int. Cl.
| | |
|---|---|
| *C08J 3/075* | (2006.01) |
| *C08B 37/00* | (2006.01) |
| *C08J 3/24* | (2006.01) |
| *C08L 5/04* | (2006.01) |
| *C08L 71/02* | (2006.01) |
| *C12N 5/00* | (2006.01) |
| *C12N 5/0775* | (2010.01) |
| *C12N 5/078* | (2010.01) |
| *C12N 5/0783* | (2010.01) |

(52) U.S. Cl.
CPC ........... *C08J 3/075* (2013.01); *C08B 37/0084* (2013.01); *C08J 3/245* (2013.01); *C08L 5/04* (2013.01); *C08L 71/02* (2013.01); *C12N 5/0018* (2013.01); *C08J 2305/04* (2013.01); *C08L 2203/02* (2013.01); *C12N 5/0636* (2013.01); *C12N 5/0644* (2013.01); *C12N 5/0662* (2013.01)

(58) Field of Classification Search
CPC ....... C08J 3/075; C08J 3/245; C08B 37/0084; C08L 5/04
See application file for complete search history.

(56) References Cited

U.S. PATENT DOCUMENTS

| | | | |
|---|---|---|---|
| 5,837,747 A * | 11/1998 | Soon-Shiong | A61L 24/08 522/75 |
| 6,224,893 B1 | 5/2001 | Langer et al. | |
| 6,497,902 B1 | 12/2002 | Ma | |
| 6,642,363 B1 | 11/2003 | Mooney et al. | |
| 7,824,672 B2 | 11/2010 | Chaikof et al. | |
| 8,216,558 B2 | 7/2012 | Van et al. | |
| 8,591,950 B2 | 11/2013 | Bennett et al. | |
| 11,655,343 B2 | 5/2023 | Garigapati et al. | |
| 12,097,306 B2 | 9/2024 | Garigapati et al. | |
| 2002/0037308 A1 | 3/2002 | Sefton et al. | |
| 2007/0048291 A1 | 3/2007 | Mang et al. | |
| 2009/0220607 A1 | 9/2009 | Kiser et al. | |
| 2010/0143464 A1 | 6/2010 | Stabler et al. | |
| 2011/0111033 A1* | 5/2011 | Stover | C08B 37/0084 424/487 |
| 2014/0147483 A1* | 5/2014 | Hubbell | A61K 35/39 424/423 |
| 2015/0071997 A1 | 3/2015 | Garcia et al. | |
| 2015/0290327 A1 | 10/2015 | Zenobi-Wong et al. | |
| 2015/0328314 A1* | 11/2015 | Friedman | A61N 5/062 530/304 |
| 2017/0182220 A1 | 6/2017 | Song et al. | |
| 2017/0189581 A1* | 7/2017 | Desai | A61L 27/52 |
| 2017/0313827 A1 | 11/2017 | Zhu et al. | |
| 2018/0296488 A1 | 10/2018 | Weitz et al. | |
| 2019/0100628 A1 | 4/2019 | Garigapati et al. | |
| 2019/0365955 A1 | 12/2019 | Garigapati et al. | |
| 2023/0348675 A1 | 11/2023 | Garigapati et al. | |
| 2024/0091414 A1 | 3/2024 | Garigapati et al. | |

FOREIGN PATENT DOCUMENTS

| | | |
|---|---|---|
| CA | 2837558 C | 11/2018 |
| CN | 1703175 A | 11/2005 |
| CN | 102164580 A | 8/2011 |
| CN | 102239248 A | 11/2011 |
| CN | 104292454 A | 1/2015 |
| CN | 104487093 A | 4/2015 |
| CN | 104530441 A | 4/2015 |
| JP | 11-509833 A | 8/1999 |
| JP | 2001-524136 A | 11/2001 |
| JP | 2006-503080 A | 1/2006 |
| JP | 2009-535453 A | 10/2009 |
| JP | 2011-246714 A | 12/2011 |
| JP | 6829898 B2 | 1/2021 |

(Continued)

OTHER PUBLICATIONS

Mahou, Macromolecules, 43, 3, 2010 (Year: 2010).*
International Search Report and Written Opinion mailed Oct. 19, 2017, for Application No. PCT/US2017/023371.
International Preliminary Report on Patentability mailed Oct. 4, 2018, for Application No. PCT/US2017/023371.
Extended European Search Report for Application No. 22184214.9, mailed Feb. 14, 2023.
Barker et al., Biodegradable DNA-enabled poly(ethylene glycol) hydrogels prepared by copper-free click chemistry. J Biomater Sci Polym Ed. 2016;27(1):22-39. doi: 10.1080/09205063.2015. 1103590. Epub Nov. 6, 2015.

(Continued)

*Primary Examiner* — Robert A Wax
*Assistant Examiner* — William Craigo
(74) *Attorney, Agent, or Firm* — Wolf, Greenfield & Sacks, P.C.

(57) ABSTRACT

The present application provides a semi-permeable hydrogel composition comprising an alginate matrix that is covalently crosslinked in its periphery to a multi-armed water soluble polymer, along with related methods and uses thereof.

20 Claims, 8 Drawing Sheets

(56) References Cited

FOREIGN PATENT DOCUMENTS

| | | |
|---|---|---|
| WO | WO 94/12161 A1 | 6/1994 |
| WO | WO 96/31199 A1 | 10/1996 |
| WO | WO 98/12228 A1 | 3/1998 |
| WO | WO 2004/032881 A2 | 4/2004 |
| WO | WO 2007/127277 A2 | 11/2007 |
| WO | WO 2010/033611 A1 | 3/2010 |
| WO | WO 2010/064171 A1 | 6/2010 |
| WO | WO 2010/099818 A1 | 9/2010 |
| WO | WO 2014/022501 A2 | 2/2014 |
| WO | WO 2014/034884 A1 | 3/2014 |
| WO | WO 2014/041231 A1 | 3/2014 |
| WO | WO 2015/067763 A1 | 5/2015 |
| WO | WO 2015/130878 A1 | 9/2015 |
| WO | WO 2015/154078 A1 | 10/2015 |
| WO | WO 2016/159380 A1 | 10/2016 |
| WO | WO 2017/042301 A1 | 3/2017 |
| WO | WO 2017/165389 A2 | 9/2017 |
| WO | WO 2018/112026 A1 | 6/2018 |

OTHER PUBLICATIONS

Blasi et al., Conformal polymer coatings for pancreatic islets transplantation. Int J Pharm. Jan. 20, 2013;440(2):141-7. doi: 10.1016/j.ijpharm.2012.10.010. Epub Oct. 16, 2012.

Dawson et al., Drug delivery: Leukocyte-like carriers. Nat Mater. Aug. 24, 2016;15(9):935-6. doi: 10.1038/nmat4737.

Feng et al., Methacrylate polymer layers bearing poly(ethylene oxide) and phosphorylcholine side chains as non-fouling surfaces: in vitro interactions with plasma proteins and platelets. Acta Biomater. Oct. 2011;7(10):3692-9. doi: 10.1016/j.actbio.2011.06.007. Epub Jun. 13, 2011.

Gattas-Asfura et al., Covalent layer-by-layer assembly of hyperbranched polymers on alginate microcapsules to impart stability and permselectivity. J Mater Chem B. Dec. 14, 2014;2(46):8208-8219.

Green et al., Adult stem cell coatings for regenerative medicine. Mater Today. Jan. 1, 2012;15(1-2):60-6.

Guanming et al., Synthesis of Hydrogels via Copper-Free Click Reactions. Progress in Chemistry. 2014; 26(7): 1223-32.

Guedes et al., Encapsulation of Living Leishmania Promastigotes in Artificial Lipid Vacuoles. PLOS One. Aug. 4, 2015;10(8):e0134925. 12 pages. doi: 10.1371/journal.pone.0134925.

Kailasapathy, Microencapsulation of probiotic bacteria: technology and potential applications. Curr Issues Intest Microbiol. Sep. 2002;3(2):39-48.

Kolb et al., Click Chemistry: Diverse Chemical Function from a Few Good Reactions. Angew Chem Int Ed Engl. Jun. 1, 2001;40(11):2004-2021. doi: 10.1002/1521-3773(20010601)40:11<2004::AID-ANIE2004>3.0.CO;2-5.

Li et al., A novel system for water soluble protein encapsulation with high efficiency: "micelles enhanced" polyelectrolyte capsules. J Biomed Mater Res A. Jun. 1, 2008;85(3):768-76.

Liu et al., Biodegradable poly(ethylene glycol)-peptide hydrogels with well-defined structure and properties for cell delivery. Biomaterials. Mar. 2009;30(8):1453-61. doi: 10.1016/j.biomaterials.2008.11.023. Epub Dec. 20, 2008.

Ma et al., Artificial microniches for probing mesenchymal stem cell fate in 3D. Biomater Sci. Nov. 30, 2014;2(11):1661-1671. doi: 10.1039/c4bm00104d. Epub Jun. 18, 2014.

Mahou et al., Alginate-Poly(ethylene glycol) Hybrid Microspheres with Adjustable Physical Properties. Macromolecules. Jan. 13, 2010;43(3):1371-8.

Mao et al., Deterministic encapsulation of single cells in thin tunable microgels for niche modelling and therapeutic delivery. Nat Mater. Feb. 2017;16(2):236-243. doi: 10.1038/nmat4781. Epub Oct. 31, 2016.

Martin et al., Microencapsulation of bacteria: A review of different technologies and their impact on the probiotic effects. Innov Food Sci Emerg Technol. Feb. 1, 2015;27:15-25.

May, Conformal coating of mammalian cells at a liquid-liquid interface. University of Toronto. 1999. Thesis. 313 pages.

Moreau et al., Hydrogel films and coatings by swelling-induced gelation. Proc Natl Acad Sci U S A. Nov. 22, 2016;113(47):13295-13300. Epub Nov. 7, 2016.

No Author Listed, Examination Handbook of Patent and Utility Model in Japan. Part II, Chapter 2, sections 2203-2205. 23 pages.

Onoe et al., Centrifuge-based cell encapsulation in hydrogel microbeads using sub-microliter sample solution. RSC Adv. 2014;4(58):30480-4.

Patel et al., Development and evaluation of a calcium alginate based oral ceftriaxone sodium formulation. Prog Biomater. 2016;5:117-133. doi: 10.1007/s40204-016-0051-9. Epub Jul. 20, 2016.

Rathore et al., Microencapsulation of microbial cells. J Food Eng. May 1, 2013;116(2):369-81.

Ribeiro et al., Temporary Single-Cell Coating for Bioprocessing with a Cationic Polymer. ACS Appl Mater Interfaces. Apr. 19, 2017;9(15):12967-12974. doi: 10.1021/acsami.6b16434. Epub Apr. 4, 2017.

Richardson et al., Fluidized bed layer-by-layer microcapsule formation. Langmuir. Aug. 26, 2014;30(33):10028-34. doi: 10.1021/la502176g. Epub Aug. 12, 2014.

Tomei et al., Device design and materials optimization of conformal coating for islets of Langerhans. Proc Natl Acad Sci U S A. Jul. 22, 2014;111(29):10514-9. doi: 10.1073/pnas.1402216111. Epub Jun. 30, 2014.

Van Dijk et al., Synthesis and characterization of enzymatically biodegradable PEG and peptide-based hydrogels prepared by click chemistry. Biomacromolecules. Jun. 14, 2010;11(6):1608-14. doi: 10.1021/bm1002637.

Xu et al., Cytocompatible poly(ethylene glycol)-co-polycarbonate hydrogels cross-linked by copper-free, strain-promoted click chemistry. Chem Asian J. Oct. 4, 2011;6(10):2730-7. doi: 10.1002/asia.201100411. Epub Aug. 24, 2011.

Zia et al., Alginate-Poly(Ethylene) Glycol and Poly(Ethylene) Oxide Blend Materials. Chapter 16. Algae Based Polymers, Blends, and Composites. Dec. 2017;581-601. DOI:10.1016/B978-0-12-812360-7.00016-1.

Dang et al., Biocompatible and antifouling coating of cell membrane phosphorylcholine and mussel catechol modified multi-arm PEGs. J Mater Chem B. Mar. 21, 2015;3(11):2350-2361. doi: 10.1039/c4tb02140a. Epub Feb. 13, 2015.

Yang et al., Phosphorylcholine-containing polymers for use in cell encapsulation. Artif Cells Blood Substit Immobil Biotechnol. Feb. 2004;32(1):91-104. doi: 10.1081/bio-120028671.

Yigit et al., Fabrication and functionalization of hydrogels through "click" chemistry. Chem Asian J. Oct. 4, 2011;6(10):2648-59. doi: 10.1002/asia.201100440. Epub Aug. 29, 2011.

\* cited by examiner

ALGINATE HYDROGEL COMPOSITIONS

RELATED APPLICATIONS

This application is a division of and claims priority under 35 U.S.C. § 120 to U.S. patent application Ser. No. 16/086,405, filed Sep. 19, 2018, which is a national stage filing under 35 U.S.C. § 371 of International PCT Application, PCT/US2017/023371, filed Mar. 21, 2017, which claims priority under 35 U.S.C. § 119 (e) to U.S. Provisional Application No. 62/312,998, titled "ALGINATE HYDROGEL COMPOSITIONS" filed on Mar. 24, 2016. The entire contents of each of which are herein incorporated by reference.

FIELD OF THE INVENTION

The disclosure relates generally to alginate-based hydrogel compositions, and their related forms, methods and uses, among other things.

BACKGROUND

Alginates are a family of naturally occurring linear anionic polymers typically obtained from brown seaweed and containing blocks of (1,4)-linked β-D-mannuronate (M) and α-L-guluronate (G) residues. Due at least in part to its biocompatibility, relatively low cost, and natural abundance, alginate has been used in a number of biomedical applications, including wound healing, delivery of bioactive agents, and cell transplantation, among others.

The structure of alginate comprises blocks of consecutive G residues, blocks of consecutive M residues, and blocks of alternating G and M residues. Biosynthetically prepared bacterial alginate, e.g., from *Azotobacter* and *Pseudomonas*, is also available. Alginates used in biomedical applications are typically in the form of a hydrogel, e.g., an ionically crosslinked hydrogel. To prepare such gels, an aqueous solution of alginate is typically combined with an ionic cross-linking agent, e.g., a divalent cation such as $Ca^{2+}$. Gel formation is driven by interactions between the G-blocks which associate to form junctions in the presence of divalent cations (Sikorski, P., et al., *Biomacromolecules*, 2007, 8:2098-2103). MG blocks also participate (Donati, I., et al., *Biomacromolecules*, 2005, 6: 1031-1040).

One drawback of ionically crosslinked alginate gels is their limited stability under physiological conditions. Ionically crosslinked gels tend to dissolve under physiological conditions by virtue of exchange reactions with monovalent and other cations. Thus, it would be highly advantageous to provide alginate compositions suitable for use in biomedical applications, but without the instability and other drawbacks associated with ionically-crosslinked and other modified alginate hydrogels.

BRIEF SUMMARY OF THE INVENTION

In a first aspect, provided herein is a semi-permeable hydrogel composition comprising an alginate matrix covalently crosslinked in the periphery of the alginate matrix to a multi-armed water soluble polymer.

In one or more embodiments, the multi-armed water soluble polymer penetrates the periphery of the alginate matrix.

In some embodiments, the periphery of the alginate matrix is interlocked with and covalently crosslinked to the multi-armed water soluble polymer.

In some additional embodiments, the hydrogel composition further comprises one or more interpenetrating (e.g., up to about 100 microns, up to about 10 microns, up to about 1 micron) surface layers of alginate that is/are covalently crosslinked to a multi-armed water soluble polymer.

In some further embodiments, the hydrogel composition further comprises a biocompatible surface layer.

In some embodiments related to the foregoing, the biocompatible surface layer is covalently bonded to the semi-permeable hydrogel composition.

In some additional embodiments, the hydrogel composition is stable for at least 30 days at 40° C. in 1 mM phosphate buffered saline.

In some further embodiments, the hydrogel composition maintains its shape when stored for 30 days at 40° C. in 1 mM phosphate buffered saline.

In yet some further embodiments, the composition is characterized by a first tan delta value determined at the time the composition is subjected to storage at 40° C. in 1 mM phosphate buffered saline (day 0), and a second tan delta value determined after the composition has been stored for 30 days at 40° C. in 1 mM phosphate buffered saline; wherein the first tan delta value and the second tan delta value are the same or differ by no more than about 0.05.

In yet some other embodiments, the hydrogel maintains its semi-permeability after storage for 30 days at 40° C. in 1 mM phosphate buffered saline.

In some additional embodiments, the composition is permeable to molecular species that have a molecular weight of about 100 kDa or less, and is impermeable to larger molecular species.

In yet some further embodiments, the alginate matrix comprises divalent or multivalent cations.

In some embodiments, related to the foregoing, the alginate matrix comprises a divalent cation selected from the group consisting of $Ca^{2+}$, $Cu^{2+}$, $Ba^{2+}$, $Sr^{2+}$, $Mg^{2+}$, and combinations thereof.

In one or more embodiments, the multi-armed water soluble polymer is a multi-armed polyethylene glycol having from 3 to 10 arms (e.g., selected from 3, 4, 5, 6, 7, 8, 9, and 10).

In some additional embodiments, the multi-armed water soluble polymer has a weight average molecular weight in a range from about 1,000 to about 100,000 Daltons.

In yet some further embodiments, the alginate matrix has a weight average molecular weight in a range from about 10,000 to about 300,000 g/mol.

Yet in some additional embodiments, the covalent crosslinks comprise covalent bonds formed by reaction of the multi-armed water soluble polymer comprising a first functional group comprised on a polymer arm (e.g., at a terminus or as a pendant group) with a second functional group on the alginate matrix, wherein the first and second functional groups are selectively chemically reactive with each other under mild reaction conditions.

In some embodiments related to the foregoing, the alginate matrix comprises from about 3 mol % to about 50 mol % of the second functional group.

In one or more particular embodiments of the first and second functional groups, the second functional group is selected from azide and tetrazine; the first functional group is selected from a dibenzyl cyclooctyne amine and norborene; and the covalent crosslinks are formed by virtue of a cycloaddition reaction between the first and second functional groups.

In one or more further embodiments of the first and second functional groups, the second functional group is selected from a dibenzyl cyclooctyne amine and norborene; the first functional group is selected from azide and tetrazine; and the covalent crosslinks are formed by virtue of a cycloaddition reaction between the first and second functional groups.

In yet some further embodiments, the hydrogel composition comprises from 1 to 20 surface layers. In yet some other embodiments, the hydrogel composition comprises from 1 to 10 surface layers.

In yet some additional embodiments of the hydrogel composition, the alginate matrix comprises a pharmacologically active material.

In some alternative embodiments of the hydrogel composition, the alginate matrix comprises living cells. In some particular embodiments, the living cells are selected from the group consisting of autologous cells, allogeneic cells or xenogeneic cells.

In yet some further embodiments of the living cells comprised within the alginate matrix, the living cells are induced pluripotent stem-cell derived cells, induced pluripotent stem-cell derived pancreatic progenitor cells, platelets, T-Cells, CAR-T cells, cardiac myoblasts, genetically modified APRE-19 cells, pancreatic cells or dermal cells.

In yet additional embodiments, the living cells are hormone, cytokine, or growth factor secreting cells.

In some embodiments related to a hydrogel composition comprising an alginate matrix that comprises a pharmacologically active material, the pharmacologically active material is selected from the group consisting of proteins, polynucleotides, and small molecules.

Yet in one or more additional embodiments, the hydrogel composition is in the form of a bead, capsule, sheet, membrane, thread, fiber, filament, particle, sponge, mesh, foam, scaffold or composite of any of the foregoing.

In yet another aspect, provided is a method of preparing a hydrogel composition comprising an alginate matrix covalently crosslinked in the periphery of the alginate matrix to a multi-armed water soluble polymer. The method comprises (i) reacting an aqueous mixture comprising an alginate matrix having from about 3 mol % to about 50 mol % of a second functional group ("ALG-B") with a multi-armed water soluble polymer comprising a first functional group on one or more of its polymer arms ("POLY-A") at a temperature ranging from about 0° C. to 60° C., wherein the first and second functional groups are selectively chemically reactive under mild reaction conditions to form covalent links, C, to thereby provide a hydrogel composition comprising a first product, a semi-permeable alginate matrix covalently crosslinked in its periphery to the multi-armed water soluble polymer.

In some embodiments related to the method, the reacting step is carried out over a period of from 5 minutes to 2 hours.

In some further embodiments related to the method, the aqueous mixture comprises from about 0.5 to 25 weight percent of the alginate matrix.

In yet some additional embodiments of the method, the concentration of the multi-armed water soluble polymer in the aqueous mixture ranges from about 0.1 weight percent to about 50 weight percent.

In yet one or more further embodiments, the method further comprises separating the first product from step (i) from the aqueous mixture to provide an isolated product.

In some additional embodiments, the method further comprises washing the isolated product with an isotonic solution.

In some particular embodiments, ALG-B comprises divalent or multi-valent cations. In one or more related embodiments, the divalent or multi-valent cation is $Ca^{2+}$.

In yet some further embodiments, ALG-B has a weight average molecular weight in a range from about 10,000 to about 300,000 g/mol.

In some additional embodiments of the method, the multi-armed water soluble polymer has a weight average molecular weight in a range from 1,000 to about 50,000 daltons.

In yet some further embodiments of the method, the multi-armed water soluble polymer is a polyethylene glycol having from 3 to 10 linear polyethylene glycol arms each terminating with a first functional group. In one or more related embodiments, the first functional group is a dibenzyl cyclooctyne amine and the second functional group is azide. In yet one or more additional embodiments, the first functional group is norborene and the second functional group is thiol or tetrazine.

In some embodiments of the method, the molar ratio of the first functional group to the second functional group is greater than one, to thereby provide the first product comprising unreacted first functional groups in the covalently crosslinked periphery of the alginate matrix.

In some particular embodiments, the molar ratio of the first functional group to the second functional group A:B is in a range of about 1.1 to 5.

In some embodiments, the method further comprises reacting the first product with ALG-B in an aqueous mixture at a temperature ranging from about 0° C. to 60° C. to thereby form a second product comprising a second layer of alginate covalently crosslinked to the hydrogel surface.

In some further embodiments related to the foregoing, the method comprises further sequential additions of POLY-A or ALG-B to the second product or a sequential hydrogel product having a crosslinked surface layer.

In some embodiments, the ALG-B from step (i) comprises a pharmacologically active material encapsulated therein. In certain embodiments, the pharmacologically active material is selected from the group consisting of proteins, polynucleotides, and small molecules.

In some other embodiments, the ALG-B from step (i) comprises living cells within the hydrogel. In some particular embodiments, the living cells are autologous cells, allogeneic cells or xenogeneic cells. In some additional embodiments, the living cells are induced pluripotent stem-derived cells, induced pluripotent stem-derived pancreatic progenitor cells, platelets, T-Cells, CAR-T cells, cardiac myoblasts, genetically modified APRE-19 cells, pancreatic cells or dermal cells.

In some particular embodiments, the living cells are hormone, cytokine, pancreatic, genetically modified ARPE-19, or growth factor secreting cells.

Additional embodiments of the compositions, methods, uses and the like will be apparent from the following description, figures, examples, and claims. As can be appreciated from the foregoing and following description, each and every feature described herein, and each and every combination of two or more of such features, is included within the scope of the present disclosure provided that the features included in such a combination are not mutually inconsistent. In addition, any feature or combination of features may be specifically excluded from any embodiment of the present invention.

BRIEF DESCRIPTION OF THE FIGURES

FIG. 3A illustrates the permeability of exemplary peripherally and surface modified alginate beads having 1, 3, 5, and 7 covalently crosslinked layer(s) to 10 kD dextran-FITC when incubated in 1 mM PBS at 40° C. for 90 days as determined by confocal microscopy. FIG. 3B illustrates the impermeability of the same beads to IgG FITC under the same conditions.

DETAILED DESCRIPTION

Figure 1:
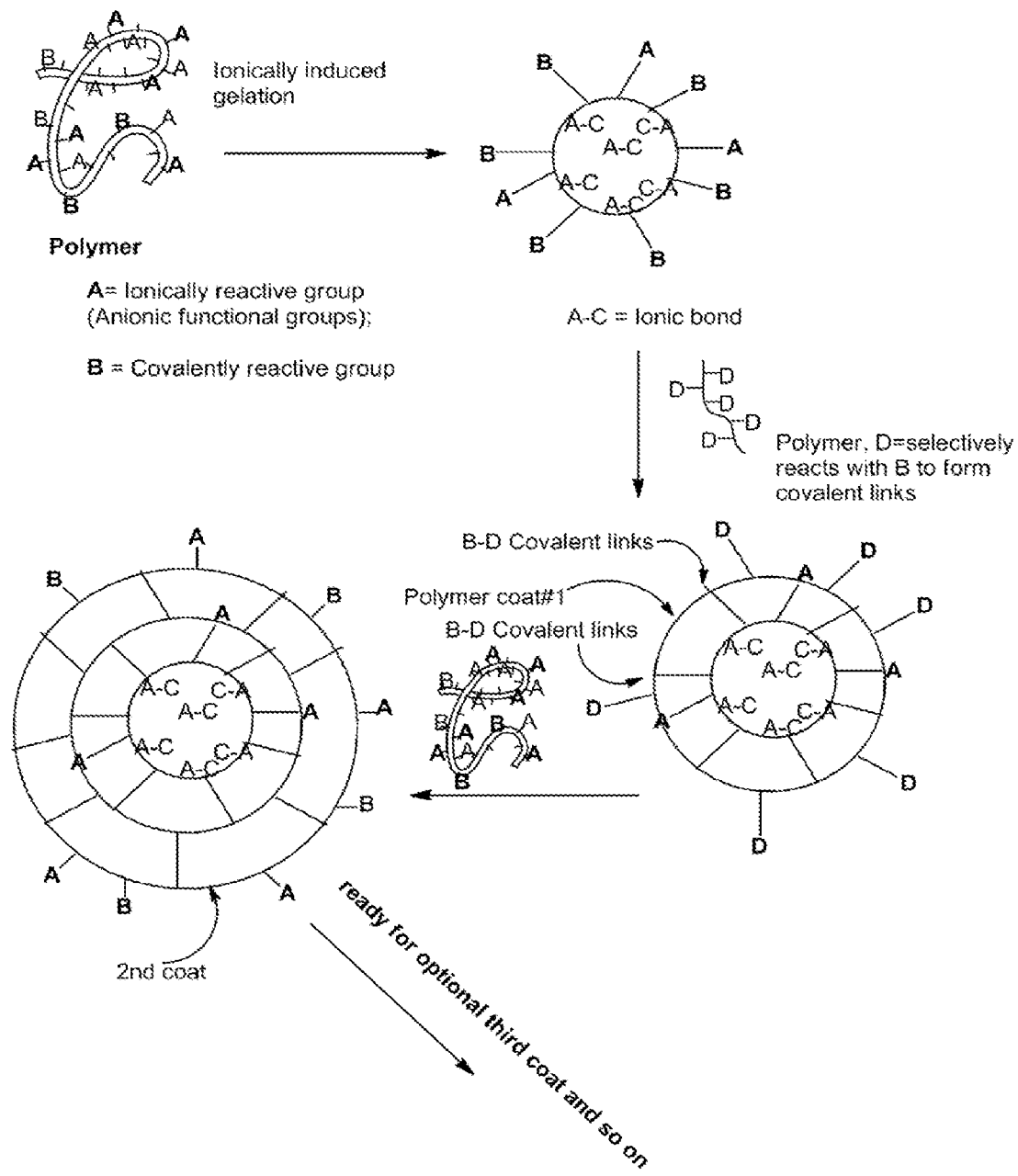
FIG. 1 provides a general schematic for preparing a semi-permeable hydrogel composition that is covalently crosslinked in its periphery, optionally comprising additional crosslinked surface layers.

The present invention now will be described more fully hereinafter. This invention may, however, be embodied in many different forms and should in no way be construed as limited to the embodiments set forth herein; rather, these embodiments are provided so that this disclosure will be thorough and complete, and will fully convey the scope of the invention to those skilled in the art.

All publications, patents and patent applications cited herein, whether supra or infra, are hereby incorporated by reference in their entirety, unless otherwise indicated. In an instance in which the same term is defined both in a publication, patent, or patent application incorporated herein by reference and in the present disclosure, the definition in the present disclosure represents the controlling definition. For publications, patents, and patent applications referenced for their description of a particular type of compound, chemistry, etc., portions pertaining to such compounds, chemistry, etc. are those portions of the document which are incorporated herein by reference.

Definitions

In describing and claiming the present invention, the following terminology will be used in accordance with the definitions described below. Unless specifically noted otherwise, definitions of the terms herein are standard definitions used in the arts of organic synthesis, and polymer and pharmaceutical science.

The singular forms "a," "an," and "the" include plural referents unless the context clearly dictates otherwise. Thus, for example, reference to a "water soluble polymer" includes a single water soluble polymer as well as two or more of the same or different water soluble polymers.

The term "about", particularly in reference to a given quantity, is meant to encompass deviations of plus or minus five percent.

The terms "alginate derivative" or "derivatized alginate" or "chemically modified alginate" refers to alginate that has been derivatized to some degree by a chemical reaction, e.g., with one or more chemical reactants.

"Alginate matrix" refers to a hydrogel comprising alginate that is electrostatically cross linked by divalent or multivalent cations. The alginate matrix can be in any desired form, such as, for example, in the form of bead, capsule, sheet, membrane, thread, fiber, filament, particle, sponge, mesh, foam, scaffold and composites of any of the foregoing, each of any desired size. (e.g., a micro-bead or a nano-bead).

"Biocompatible surface layer" as used herein refers to a layer on the surface of the hydrogel composition that comprises a biocompatible coating. The biocompatible coating is preferably covalently bonded to the hydrogel composition.

"Core" refers to that portion of an alginate matrix that is not the "periphery" as defined herein.

A "dendrimer" is a highly branched, spherical, size monodisperse polymer in which the bonds emerge radially from a central focal point or core with a regular branching pattern and with repeat units that each contribute a branch point. Dendrimers are generally characterized by having a central core, an interior dendritic structure (the branches), and an exterior surface with functional surface groups. Dendrimers exhibit certain dendritic state properties that make them unique from other types of polymers.

The terms "effective amount" or "pharmaceutically effective amount" or "therapeutically effective amount" of a composition refer to a non-toxic but sufficient amount of the composition to provide a desired response. The exact amount required will vary from subject to subject, depending on the species, age, and general condition of the subject, the severity of the condition being treated, the specifics of the composition, mode of administration, and the like. An appropriate "effective" amount in any individual case may be determined by one of ordinary skill in the art.

By "gelation" is meant the formation of a material into a gelled state.

The term "hydrogel" refers to a water-containing three dimensional hydrophilic polymer network or gel in which the water is the continuous phase.

A "hyperbranched" polymer is a highly branched polymer in which bonds emerge radially from a central core having an irregular branching pattern (in contrast to dendrimers, which have a regular branching pattern).

"Molecular mass" or molecular weight, as used herein, in the context of a water-soluble polymer such as a polyethylene glycol, refers to the number-average molecular weight, unless indicated otherwise. In the absence of a molecular weight value, a polymer may also be characterized by its intrinsic or inherent viscosity, which is a viscometric method for measuring molecular weight.

"Multi-armed" in reference to the geometry or overall structure of a water soluble polymer refers to polymer having 2 or more linear polymer chains or "arms" emanating from a central core. Thus, a multi-armed polymer may possess 2 polymer arms, 3 polymer arms, 4 polymer arms, 5 polymer arms, 6 polymer arms, 7 polymer arms, 8 polymer arms or more, depending upon its configuration and core structure. Multi-armed polymers exclude dendritic polymers or dendrimers as well as hyperbranched polymers having densely branched tree-like structures.

"Optional" or "optionally" means that the subsequently described circumstance may or may not occur, so that the description includes instances where the circumstance occurs and instances where it does not.

"Periphery" of an alginate matrix refers to the area in the matrix that includes the external surface of the matrix and extends into the matrix up to about 100 microns from the surface. In particular aspects, the "periphery" of an alginate matrix includes the external surface of the matrix and extends into the matrix up to about 10 microns from the surface, or extends into the matrix up to about 1 microns from the surface. Thus, in certain embodiments, crosslinks between the alginate matrix and multi-armed water soluble polymer in the periphery of the alginate matrix do not extend throughout the matrix, e.g., do not extend to the center of the alginate matrix.

The term "reactive" refers to a functional group (e.g., present in a polymer) that reacts readily or at a practical rate under conventional conditions of organic synthesis. This is in contrast to those groups that either do not react or require strong catalysts or impractical reaction conditions in order to react (i.e., a "nonreactive" or "inert" group).

"Semi-permeable", in reference to a hydrogel composition comprising an alginate matrix crosslinked in its periphery as provided herein, refers to a biocompatible composition that is permeable to certain materials but not to others. Illustrative hydrogels are, for example, effective to retain encapsulated cells while permitting the passage of materials and oxygen to the cells and metabolic materials from the cells.

The term "substantially" in reference to a certain feature or entity means to a significant degree or nearly completely (i.e. to a degree of 85% or greater) in reference to the feature or entity.

Where a range of values is provided, it is intended that each intervening value between the upper and lower limit of that range and any other stated or intervening value in that stated range is encompassed within the disclosure. For example, if a range of from 3 mol % to 10 mol % is described, it is intended that 3 mol %, 4 mol %, 5 mol %, 6 mol %, 7 mol %, 8 mol %, 9 mol %, and 10 mol % are also explicitly disclosed, as well as the range of values greater than or equal to 3 mol % and the range of values less than or equal to 10 mol %.

Reference to an organic compound is meant to include the compound in any of its acceptable forms, including isomers such as diastereomers and enantiomers, salts, solvates, and polymorphs, particular crystalline forms, as well as racemic mixtures and pure isomers of the compounds described herein, where applicable.

Additional definitions may also be found in the sections which follow.

Overview

The present application is based, at least in part, on the inventors' discovery of among other things, a semi-permeable hydrogel composition having a number of particularly surprising and beneficial features, which are described in greater detail herein. The hydrogel composition comprises an alginate matrix that is covalently crosslinked in its periphery to a multi-armed water soluble polymer. In one or more embodiments, the multi-armed water soluble polymer penetrates the periphery of the alginate matrix, to thereby provide a composition wherein the periphery of the alginate matrix is interlocked with and covalently crosslinked to the multi-armed water soluble polymer. This stabilizes the hydrogel and, thereby, imparts several unique and surprising features to the instant compositions.

Further to this point, based upon characterization of the instant hydrogel compositions, it has been recognized that in contrast to other known seemingly-stabilized alginates, the instant compositions maintain their shape and gel integrity (i.e., have good mechanical stability), and also retain their semi-permeability and other rheological properties, for an extended period of time when placed under high stress conditions modeling an in vivo environment. More specifically, exemplary alginate hydrogel formulations having a covalently crosslinked periphery, and optionally additional surface layers, maintained their shape (e.g., bead shape) and integrity for up to at least 90 days when stored in 1 mM PBS at 40° C. This was particularly surprising, since it was well-known that alginate hydrogels swell when stored in PBS, particular at an elevated temperature, and the ions contained in PBS (e.g. phosphate ions) displace the cations in the alginate hydrogel ultimately resulting in breakage and collapse of the hydrogel matrix. These same exemplary alginate hydrogel formulations also maintained their semi-permeability under simulated in vivo conditions for an extended period of time, i.e., for at least 30 days, and indeed up to 3 months. Thus, the inventors have discovered alginate hydrogel compositions that have superior stability (structural and functional resiliency). By virtue of the foregoing, the instant alginate hydrogel compositions are advantageously suited for use in therapeutic products, and in particular, for delivering viable cells, among other uses.

The stability of the alginate hydrogel compositions was achieved in hydrogel beads having a covalently crosslinked periphery without the inclusion of additional covalently crosslinked surface layers, as well as for those having multiple covalently crosslinked surface layers. This demonstrates the efficacy of both the covalently crosslinked periphery (e.g., periphery of the alginate matrix is interlocked with and covalently crosslinked to the multi-armed water soluble polymer) and of multiple covalently crosslinked surface layers.

Without being bound by any particular theory, the striking stability of the instant hydrogels (e.g., retained structural integrity and semi-permeability under simulated in vivo conditions), is believed to arise, at least in part, from the covalent crosslinked periphery of the alginate matrix, which is believed to include covalent bonds between the multi-armed water soluble polymer that inter-penetrate to a degree below the surface of the alginate matrix, and the alginate matrix. This physico-chemical feature is inferred from dynamic mechanical analysis data, and in particular, the tan delta, which provides a measure of the energy dissipation of a material. For the instant hydrogels, the tan delta is significantly lower (i.e., several-fold lower) than for other "stabilized" alginate hydrogels such as alginate-poly-L-ornithine-alginate (also referred to as APA), indicating their order and limited pliability. It is further inferred from mechanical stability data and the nature of the covalent crosslinking that the instant hydrogels do not merely possess a surface coating, but rather, contain covalent crosslinks in the periphery of the alginate matrix below the outer surface of the alginate matrix. It is believed that this results in the achieved structural stability and functional stability (e.g., semi-permeability), even when the hydrogels are placed under high stress conditions.

Finally, the hydrogels are formed under mild reaction conditions—without the need for initiators or accelerants or other deleterious additives. The features of the hydrogel composition, its components, related methods, uses and the like will now be discussed in greater detail below.

Semi-Permeable Hydrogel Composition

Alginate/Alginic Acid

The hydrogel composition comprises an alginate matrix. The alginate (alginic acid) may be obtained from any suitable source, including both algael and bacterial sources including, for example, *Laminaria hyperborea, Laminaria digitata, Laminaria japonica, Ascophyllum nodosum*, and *Macrocystis pyrifera*, as well as *Azotobacter* and *Pseudomonas*; alginate is most commonly sourced from brown algae. Alginates obtained from bacterial sources are partially acetylated. Alginates suitable for use in preparing a hydrogel composition as provided herein include, for example, those described in Tonnesen, H., et al., *Drug Dev Ind. Pharm.*, 2002; 28:621-630. Alginate comprises blocks of (1,4)-linked β-D-mannuronate (M) and α-L-guluronate (G) residues; alginates for use herein may possess any suitable ratio of M/G blocks. For example, the G-block content may range from about 10% up to about 80%, or may range from about 10% to about 60%, or from about 15% to about 50%, or from about 20% to about 80%, or from about 20% to about 60%, or from about 20% to about 55%. In some embodiments, the G-block content is in a range from about 30% to about 95%, or in some preferred embodiments, is in a range from about 40% to about 70%. M and G unit content is typically provided by the manufacturer, and can also be determined by $^1$H NMR spectroscopy. The alginate will typically possess an average molecular weight (weight average) in a range from about 5,000 to about 500,000 g/mol, or from about 7,000 to about 400,000 g/mol, or from about 10,000 to about 300,000 g/mol. In some embodiments, a preferred molecular weight range is from about 10,000 daltons to about 300,000 daltons. Alginates used to prepare the alginate matrix may be the same or different from the alginates used to provide the covalently crosslinked surface layers.

The alginate (or alginic acid, depending upon pH) is functionalized to introduce a functional group that is reactive with a complementary functional group on a multi-armed water soluble polymer. Any number of combinations of reactive functional groups can be used to prepare the instant hydrogels; preferred reaction pairs are those resulting in a stable covalent linkage, i.e., one that is not rapidly hydrolyzed in vivo or under simulated in vivo conditions. For instance, the alginate may be functionalized, either directly or via a linking moiety, to introduce a reactive functional group such as, for example, amino, activated carboxy groups such as N-succinimidyl carbonate, hydrazide, succinimidyl propionate, succinimidyl butanoate, succinimidyl succinate, benzotriazole carbonate, glycidyl ether, oxycarbonylimidazole, p-nitrophenyl carbonate, maleimide, orthopyridyl disulfide, acrylol, vinylsulfone, thiol groups, aldehydes, and the like. In one or more embodiments, alginate derivatization is carried out by reaction with a difunctional linker. Alginate functionalization is typically carried out by reaction with alginate carboxyl groups. The particular reaction pairs and chemistries employed should not be considered limiting, and will be known to those of skill in the art. As an example, active esters such as succinimidyl esters react with amino groups to form amides; benzotriazole carbonate reacts with amino groups to form carbamates; maleimides, vinyl sulfones, haloacetyl, pyridyldisulfide, thiosulfonate, and thiols react with thiol groups; aldehydes react with primary amino groups under reduction amination conditions to form secondary amines, and so forth.

Reactive functional groups that can be used to provide the instant hydrogels having covalent crosslinks in the periphery, as defined herein, also include those associated with click chemistry or Staudinger ligation. Suitable click chemistry reactions include cycloadditions such as 1,2-dipolar cycloadditions and hetero-Diels alder cycloadditions; nucleophilic ring openings of strained heterocyclic electrophiles such as aziridines, epoxides, cyclic sulfates, episulfonium, etc.; non-aldol carbonyl chemistry to form ureas, thioureas, hydrozones, oxime ethers, amides and aromatic heterocycles; and additions to carbon-carbon multiple bonds, such as epoxidations, aziridinations, dihydroxylations, sulfenyl halide additions, nitrosyl additions, and Michael additions. Click chemistry reaction pairs, i.e., those that are selectively reactive under mild conditions, relatively fast, regiospecific, form by-products that are readily removed, and that result high product yields, are particularly preferred in those embodiments in which the alginate matrix contains living cells. Illustrative preferred selective functional group pairs for covalent coupling include azide-DBCO (dibenzocyclooctyne) (resulting in a triazole linkage), thiol-norborene (Michael addition), and tetrazine-norborene (pyrazo linkage). In one or more embodiments, the covalent attachment between the alginate and the multi-armed water soluble polymer is a cycloaddition reaction between an azide and a terminal alkyne to form a 1,2,3-triazole. In some additional embodiments, the covalent attachment between the alginate and the multi-armed water soluble polymer is a Diels-Alder reaction. In yet some further embodiments, the covalent attachment between the alginate and the multi-armed water soluble polymer takes place via a Michael addition. Illustrative reaction pairs that may be employed are described in, for example, McKay, C., et al., *Chemistry & Biology*, 21 (9), 18 Sep. 2014, 1075-1101; *Click Chemistry for Biotechnology and Materials Science*, J. Lahann, Ed., John Wiley & Sons, 2009 (including the references provided therein). The selective functional group pairs described above are interchangeable, i.e., may be comprised in the derivatized alginate or in the multi-armed water soluble polymer.

Functionalization of an alginate may be direct, i.e., the carboxyl groups may be directly transformed to a functional group suitable for reaction with a multi-armed water soluble polymer, or may be via a linker. Typically, an alginate is derivatized by reaction with a difunctional linker having a length of from about 2 to about 20 atoms, or from about 2 atoms to about 15 atoms, or from about 2 to 10 atoms, where one terminus of the linker is a functional group suitable for selective reaction with the multi-armed water soluble polymer, and the other terminus is suitable for selective reaction with alginate carboxyl groups. For example, one exemplary linker described in the Examples (see, e.g., Example 1) is 3-azido-aminopropane, where the amino group selectively reacts with alginate C-6 carboxyl groups to form an amide, while the azide functionality is used for covalent attachment to a suitably functionalized multi-armed water soluble polymer. When considering atom chain length, atoms contributing to the overall distance are considered. For example, a 3-azido-aminopropane linker having the structure, $NH_2$—$CH_2$—$CH_2$—$CH_2$—N=N=N, has a chain length of 7 atoms, since substituents are not considered to contribute significantly to the length of the linker. Typical difunctional linkers are linear, comprising aliphatic chains, e.g., a bivalent saturated aliphatic radical such as alkylene (—$CH_2$-$CH_2$)$_n$, where n is typically in a range of 1 up to about 10, connecting the terminal reactive functional groups. Alternatively, any suitable linker may be employed; small linear oligomeric ethylene glycols functionalized at both termini may be used as linkers, ~(PEG~)$_n$, where n ranges from about 1-7 (e.g., is 1, 2, 3, 4, 5, 6, or 7). In some embodiments, preferred bifunctional linkers possess an amino group at one terminus (i.e., suitable for reaction with alginate carboxyls), while the other terminus possesses a functional group suitable for selective covalent reaction with the multi-armed water soluble polymer.

An alginate is typically derivatized such that an average of between 2 mol % to about 80 mole %, or from about 3 mol % to about 60 mol %, or from about 3 mol % to about 50 mol % of alginate carboxyl groups are derivatized by reaction with a carboxyl-selective functional group of the bifunctional linker. The degree of alginate derivatization can be controlled by the selection of alginate starting material, the nature of the coupling reaction employed, reaction conditions such as, for example, molar ratios of reactants, relative concentrations, and reaction times. Shorter reaction times will result in lower degrees of alginate derivatization. As an illustration, Example 1 describes modification of alginate by reaction with an illustrative bifunctional linker, 3-azido-aminopropane, to provide alginate having 20% substitution, 15% substitution, 10% substitution, and 5% substation, where the degree of substitution was adjusted by adjusting the number of equivalents of bifunctional linker. Illustrative degrees of alginate substitution with the bifunctional linker are selected from the following mole percentages: 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, and so forth, along with ranges resulting from each and every combination of integers provided, e.g., from 2-15%, from 15-20%, from 20-25%, from 25-30%, from 30-35%, from 35-40%, from 40-45%, from 45-50%, and so forth.

The degree of substitution/modification of alginate can be determined by any of a number of suitable methods, e.g., NMR, UV, or IR analysis, or elemental analysis. A preferred method for calculating percent substitution of a polymer such as alginate is $^1$H NMR.

Figure 7A:
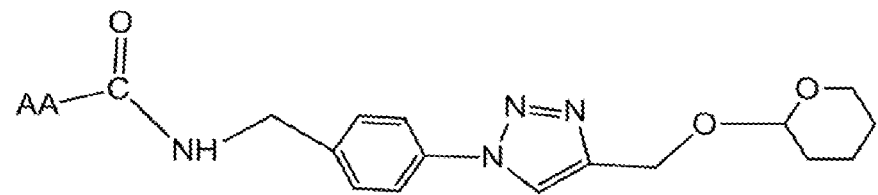
FIGS. 7A-7C provide exemplary moieties for introducing fibrosis-resistance to the instant alginates, where AA represents alginic acid/alginate, and n ranges from about 1-10, and in some embodiments is 3.
Figure 7B:
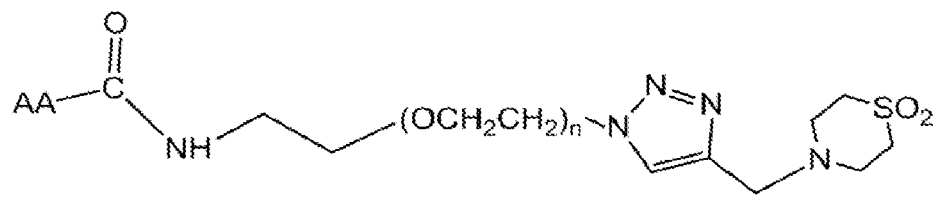
Figure 7C:
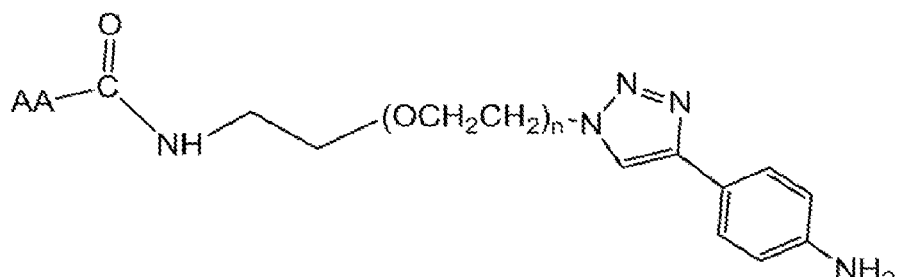

The alginate may optionally be further modified to comprise additional functionalities effective to resist/mitigate implant fibrosis and/or to provide hydrogels having reduced subcutaneous inflammation, or more generally, which exhibit a minimal immune response. Modification can be carried out at alginate hydroxyl or carboxyl groups. In some preferred embodiments, modification to introduce moieties effective to resist or mitigate implant fibrosis occurs at alginate carboxyl functionalities, e.g., by introduction of a bifunctional molecular having, at one terminus, a functional group suitable for reaction with alginate carboxyl groups such as an amino group. Preferred moieties are those comprising a triazole group or a derivatized triazolyl group, such as, for example, a triazole group substituted with a moiety comprising a 6-membered aryl or heteroalkyl ring. Examples include triazole-thiomorpholine dioxide, triazole-tetrahydrofuran, or triazole-aniline, to name a few. The triazole or derivatized triazolyl group may be connected to the alginate via either a hydrophilic or a hydrophobic linker. Illustrative linkers are those having, for example, alkylene (i.e., a linear alkyl chain), cycloalkylalkylene, aralkylene, or oligomeric PEG interconnecting the two reactive termini, although any suitable non-reactive linking group may be used. One representative method for introducing such moieties is via a Huisgen cycloaddition between an azide and an alkyne to form the desired triazolyl group. Representative moieties and chemical synthetic methodologies for forming triazolyl or similarly modified alginates having minimized or reduced recognition by macrophages and/or minimized or reduced fibrous deposition are described in, e.g., Vegas, A., et al., *Nature Biotechnology*, including supplementary materials (published online 25 Jan. 2016). See, e.g., FIG. 1 and FIG. 2e. Representative functional groups include N-(4-(4-(((tetrahydro-2H-pyran-2yl)oxy)methyl-1H-1,2,3-triazol-1-yl)benzylcarboxamide; N-(2-(2-(2-((4-((1,1-dioxidothio-morpholino)methyl)-1H-1,2,3-triazol-1-yl)methoxy) ethoxy)ethyl)carboxamide; and N-(2-(2-(2-((4-(4-aminophenyl)1H-1,2,3-triazol-1-yl)methoxy)ethoxy)ethyl) carboxamide as shown in FIGS. 7A-C, where AA indicates alginic acid/alginate, and n ranges from 1-10, and in some embodiments, is 3. The alginate can be modified to any suitable degree, depending on the position and type of alginate chemical modification used to introduce the functionalities suitable for covalent crosslinking, and the degree of substitution of such crosslinkable functionalities.

Such functionalized alginate having any combination of features described above (extent of modification, bifunctional linker, molecular weight, etc.,) is suitable for use in the compositions, kits, methods and uses provided herein.

The alginate is formed into an alginate matrix that is electrostatically crosslinked by exposure to divalent or multivalent cations. Formation of the alginate matrix containing ionic crosslinks can be carried out either prior to or subsequent to chemical modification with a bifunctional linker. Generally, formation of an alginate matrix is carried out by combining an aqueous alginate solution with ionic crosslinking agents, such as divalent or multivalent cations, to form a hydrogel. Conditions for ionic crosslinking of an aqueous alginate solution are well-known in the art. Cations suitable for promoting ionic crosslinking include, for example, $Ca^{2+}$, $Cu^{2+}$, $Ba^{2+}$, $Sr^{2+}$, $Mg^{2+}$, and mixtures thereof, which are typically added to the aqueous alginate solution in the form of a salt. Exemplary anions include halides, sulfate, and carbonate. One particularly useful ionic crosslinking agent is calcium chloride. In one or more particular embodiments, the cation is a divalent cation. In some preferred embodiments, the divalent cation is $Ca^{2+}$, or is a combination of $Ca^{2+}$ with another divalent cation such as $Ba^{2+}$ where the calcium is in molar excess of the secondary cation. Exemplary combinations of divalent cations include, for example, $Ca^{2+}:Ba^{2+}$ in a molar ratio selected from 49:1, or 45:5, 40:10, and 30:20. In one or more embodiments in which a combination of divalent cations is used, the combination is a combination of $Ca^{2+}:Ba^{2+}$ at a molar ratio of 49:1. As an illustration, Example 3 describes the preparation of ionically crosslinked alginate beads, both with and without modification with a bifunctional linker.

Multi-Arm Water Soluble Polymer

Multi-arm water soluble polymers for use in forming the instant hydrogels possess 2 or more linear polymer chains or "arms" emanating from a central core. Thus, a multi-armed polymer may possess 2 polymer arms (typically referred to as a branched polymer) with 2 linear polymer arms emanating from a single branch point, 3 polymer arms, 4 polymer arms, 5 polymer arms, 6 polymer arms, 7 polymer arms, 8 polymer arms, 9 arms or 10 arms, or more, depending upon its configuration and core structure. In some embodiments, the multi-armed water soluble polymer has from 3-10 polymer arms. In some embodiments, the multi-armed water soluble polymer has from 3-8 arms. In some embodiments, the multi-armed water soluble polymer has 4 arms. In some alternate embodiments, the multi-armed water soluble polymer has 6 arms. In some further embodiments, the multi-armed water soluble polymer has 8 arms. As described above, a multi-armed polymer is not a dendritic polymer nor a hyperbranched polymer. In some embodiments, an arm of a multi-armed polymer involved in a covalent linkage itself is not branched (i.e., is linear). For example, in some preferred embodiments, for a given functional group on the alginate involved in a covalent cross-linkage, there is a 1-1 linkage to a given arm of the multi-armed polymer.

Representative water soluble polymers include polyethylene glycol, poly(ornithine), poly(L-lysine, poly(lactic acid, poly(N-isopropylacrylamide), polypoly(olefinic alcohol), poly(vinylpyrrolidone), poly(hydroxyalkylmethacrylamide), poly(hydroxyalkylmethacrylate), poly(saccharide), poly(α-hydroxy acid), poly(acrylic acid), poly(vinyl alcohol), polyphosphazene, polyoxazoline, poly(N-acryloylmorpholine), poly(2-methacryloyloxyethyl phosphorylcholine), or copolymers or terpolymers thereof, including copolymers of (2-methacryloyloxyethyl phosphorylcholine) and L-lysine methacrylamide. In some embodiments, the multi-armed water soluble polymer is a polyethylene glycol polymer.

Multi-armed polymers such as multi-armed PEGs and other polymers are commercially available from suppliers such as, for example, Creative PEGWorks (Chapel Hill, NC), JenKem Technology USA (Plano, TX), Laysan Bio, Inc. (Arab, Alabama), and NOF America Corporation (Irvine, CA).

A central core molecule of a multi-arm polymer may be, e.g., a residue of a polyol, polythiol, polycarboxylic acid, or a polyamine, bearing at least three hydroxyl, thiol, or amino groups available for polymer attachment. Illustrative core molecules of multi-armed water soluble polymers such as PEG include, e.g., lysine, erythritol, pentaerythritol, trimethylolpropane, glycerol, glycerol dimer (3,3'-oxydipropane-1,2-diol), glycerol oligomers, sorbitol, hexaglycerol, and the like. Multi-arm PEG polymers generally possess linear polyethylene glycol arms emanating from a central core molecule, and having one or more of their polymer arms functionalized with a functional group that is covalently reactive with the functional groups present on the derivatized alginate. The functional group(s) for reaction with the alginate may be at terminus of a polymer arm or may be pendant (i.e., located on the polymer arm but not located at its terminus). In one or more embodiments, the multi-armed polymer possesses a single functional group for reaction with the alginate in each of its polymer arms, e.g., at the terminus or as a pendant functional group, or possesses on average, fewer than a single functional group for reaction with the alginate in each of its polymer arms (i.e., wherein not every polymer arm possesses a functional group for reaction with the alginate). Illustrative multi-armed PEGs include 4-arm PEG having a pentaerythritol core and end- or otherwise-functionalized with a group that is selectively reactive with functional groups on the derivatized azide. See, for example, structures of NOF's multi-armed PEG polymer Sunbright® series including 4-arm PEGs end functionalized with N-hydroxy succinidyl, para-nitrophenyl carbonate, amine, thiol, and maleimide (incorporated by reference herein), suitable for use in preparing the instant hydrogel compositions. Similarly, 4-arm PEGs end-functionalized with a variety of functional groups and intervening linkers are available from Creative PEGworks, including those having terminal reactive groups selected from hydroxyl, acrylate, acrylamide, amine, thiol, various N-hydroxy succinimides including succinimidyl carboxymethyl ester, succinimidyl glutarate ester, succinimidyl succinate ester, glutaramide succinimidyl ester, and succinamide succinimidyl ester, epoxide, para-nitrophenylcarbonate, carboxymethyl (carboxy), glutaric acid, succinic acid, glutaramide acid, succinamide acid, azide, and alkyne. Such multi-armed polymers may be used directly for forming the instant hydrogel compositions, or may be further customized, i.e., chemically modified, to provide the desired functional group(s). In one or more embodiments, the multi-armed water soluble polymer comprises a reactive group that is selected from DBCO, azide, cyclooctyne, electron-deficient alkyne, tetrazine, alkene, and thiol.

Another representative multi-arm PEG is an 8-arm PEG having a hexaglycerine core. See, for example, structures of NOF's 8-armed HGEO series of polymers, or 8-arm PEGs available from Creative PEGworks. As described above, a multi-armed water soluble polymer such as a multi-armed PEG can be chemically modified using known synthetic transformation methodologies to provide a multi-armed water soluble polymer having the desired terminal reactive groups suitable for reaction with the derivatized alginate.

The multi-arm water soluble polymer will typically possess a molecular weight ranging from about 500 to about 60,000 daltons. Illustrative molecular weight ranges are from about 1,000 to about 40,000 daltons, from about 1,000 to about 30,000 daltons, from about 1,000 to about 20,000 daltons and from about 1,000 to about 10,000 daltons. Exemplary molecular weights of the multi-armed polymer include, for example, 1 kD, 5 kD, 10 kD, 20 kD, 30 kD, 40 kD, 50 kD, and 60 kD.

Bioactive Agents and Therapeutic Cells

The hydrogels provided herein may optionally comprise a pharmacologically active material or living cells. Pharmacologically active agents include small molecules (having a molecular weight less than about 1000), proteins, polynucleotides and the like.

Pharmacologically active agents that may be comprised in the compositions provided herein include, for example, antimicrobials, antibiotics, analgesics, antibiotics, antiproliferative/antimitotic agents, enzymes, antiproliferative/antimitotic alkylating agents, antiproliferative/antimitotic antimetabolites; platinum coordination complexes, hormones, anticoagulants, fibrinolytic agents, antimigratory agents; antisecretory agents, anti-inflammatory agents, non-steroidal agents, gold compounds, immunosuppressive agents, mitogenic or morphogenic growth factor proteins, peptides or mimetics; growth factor receptor agonists or antagonists, nitric oxide donors; anti-sense oligonucleotides, transcription factors, signaling cascade mediators, and combinations thereof.

A hydrogel as provided herein may also include living cells. Such living cells may be autologous, allogeneic, or xenogenic. Exemplary living cells include, for example, stem cells, induced pluripotent cells, functionally differentiated cells, recombinant cells, or a combination thereof. Examples of stem cells include but are not limited to, embryonic stem cells such as human embryonic stem cells, hematopoietic stem cells, vascular stem cells, neural stem cells, mesenchymal stem cells, cardiac stem cells, adipose stem cells, muscular stem cells, dental stem cells, skeletal stem cells, cartilage stem cells, periosteal stem cells, mammary stem cells, uterus stem cells, endothelial stem cells, skin stem cells, placental stem cells, umbilical cord blood stem cells, yolk sac stem cells, and amniotic fluid stem cells.

Exemplary functionally differentiated cells include fibroblasts, chondrocytes, osteoblasts, osteocytes, adipocytes, epithelial cells, keratinocytes, retinal cells, dental cells, renal cells, pancreatic islet cells, hepatocytes, neuronal cells, immune cells, muscle cells, and blood cells.

In some embodiments, the living cells are selected from induced pluripotent stem (iPS)-derived cells, iPS-derived pancreatic progenitor cells, platelets, T-Cells, CAR-T cells, cardiac myoblasts, and dermal cells. In some other embodiments, the living cells are hormone, cytokine, pancreatic, genetically-modified ARPE-19, or growth factor secreting cells.

Tissue sources of stem cells include, for example, adult (e.g., hematopoietic, vascular, neural, mesenchymal, cardiac, adipose, muscular, dental, skeletal, cartilage, periosteal, mammary, uterus, skin); perinatal (e.g., placental, umbilical cord blood); fetal (e.g., amniotic fluid, yolk sac, neural, skin); and embryonic. Functionally differentiated cells may be obtained from adult human donors (autologous or allogeneic) or from animal sources (xenogeneic). Source cells can include fibroblasts, chondrocytes, osteoblasts, osteocytes, adipocytes, epithelial cells, keratinocytes, retinal cells, dental cells, renal cells, pancreatic islet cells, hepatocytes, neuronal cells, immune cells, muscle cells, and blood cells.

Additional bioactive agents include but are not limited to those which inhibit one or a combination of processes including but not limited to cell division, cell secretion, cell migration, cell adhesion, cytokine, chemokine (or other inflammatory activator) production and/or release, angiogenesis, and/or free radical formation and/or release, and/or coagulation cascade.

The compositions provided herein may also be effective to produce pharmacological alteration of cellular and/or non-cellular processes which increase the development of fibrosis. Thus, bioactive agents further include but are not limited to those which increase one or a combination of processes including but not limited to cell division, cell secretion, cell migration, cell adhesion, cytokine, chemokine (or other inflammatory activator) production and/or release, angiogenesis, and/or free radical formation and/or release. Additional bioactive agents may increase or affect other processes involved in the scarring process such that the compositions provided herein may be hemostatic agents and/or adhesion prevention agents, such that the addition of a drug can effect an increase or decrease in fibrosis, and/or result in tissue augmentation and/or increase or reduction in surgical adhesions depending on the drug mechanism.

The bioactive agent or living cells will typically be entrapped within a hydrogel composition as provided herein. Alternatively, a bioactive agent may be covalently attached, in a releasable fashion, to a component used to prepare the hydrogel, e.g., the derivatized alginate or multi-armed water soluble polymer. The hydrogel composition may comprise, for example, from about 0.001 to about 50 weight percent of an encapsulated pharmacologically active material, or from about $10^6$ to about $10^{11}$ cells per dose.

Hydrogel Composition and Method of Making

The hydrogel compositions are generally prepared as follows, although it will be appreciated that the methods described may be suitably modified by one skilled in the art to arrive at the compositions, materials, and hydrogels provided herein, based upon the instant disclosure. The instant hydrogel compositions are typically formed by reacting a derivatized alginate matrix as describe above with a multi-armed water soluble polymer under conditions effective to form an alginate matrix covalently crosslinked in its periphery to a multi-armed water soluble polymer. The alginate matrix may be sequentially modified to comprise from one to several layers of covalently attached water soluble polymer, where the polymer layers typically alternate between functionalized alginate and water soluble multi-armed polymer. Alternatively, following formation of covalent crosslinks to a multi-armed water soluble polymer on the periphery of the alginate matrix, additional interlocking layers may be covalently attached by reaction with any suitable water-soluble polymer. The reacting group pair utilized to form the covalently attached periphery of the alginate matrix can be the same or different from the reacting group pair(s) used to form optional additional covalently linked surface layers. The alginate matrix may also optionally comprise one or more moieties effective to mitigate an immune response upon administration of the hydrogel composition as described above, where such modification may be either before or after introduction of the covalently reactive crosslinkable groups. Alternatively, in some embodiments, the covalent crosslinks, e.g., those comprising a dibenzylcyclooctane triazole ring system, or a triazole group, or a modified triazole, may be effective to reduce/minimize an immune-mediated reaction upon administration of the instant hydrogel compositions to a human or animal subject.

Figure 2:
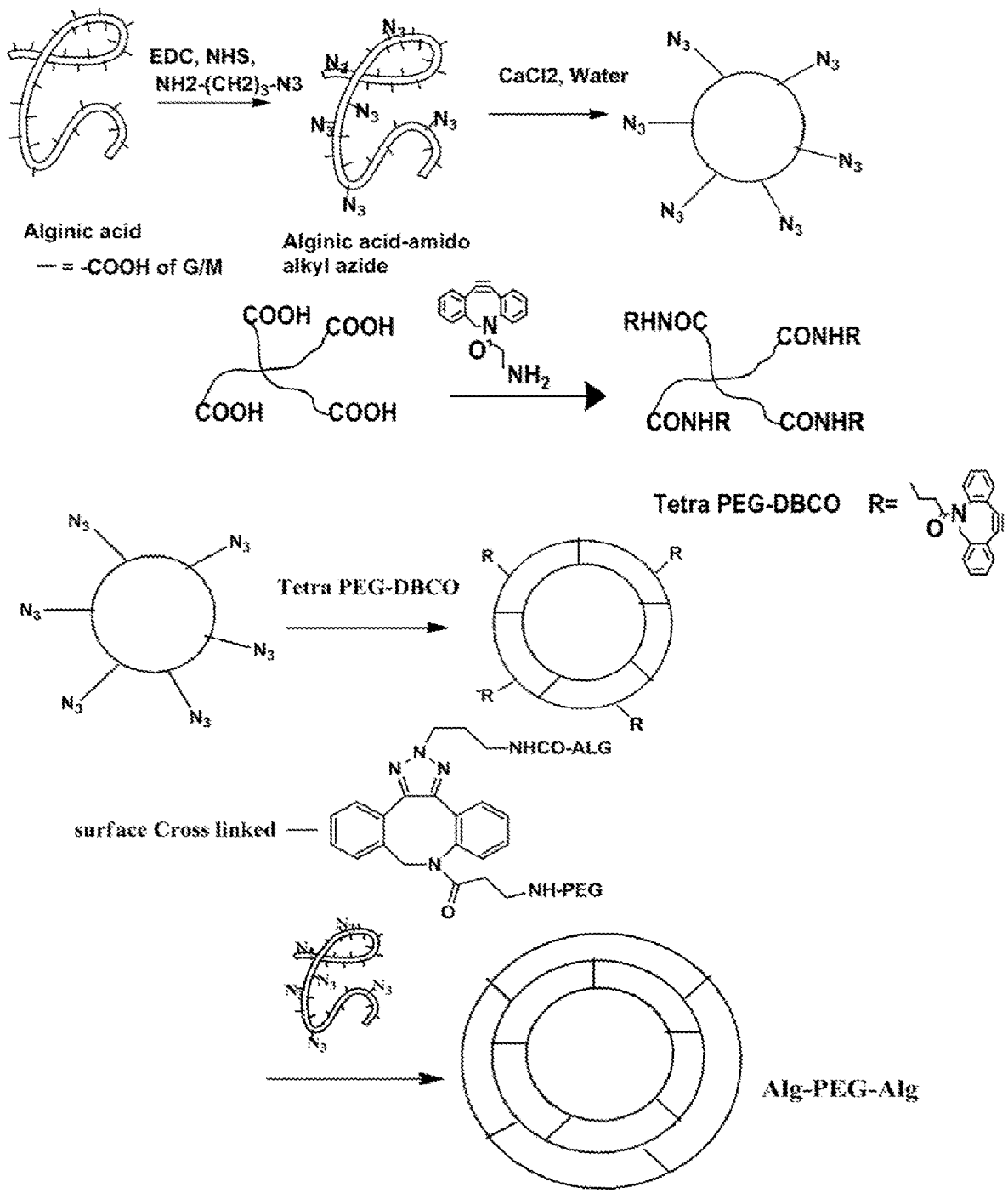
FIG. 2 provides an exemplary reaction scheme for preparing an alginate matrix that is covalently crosslinked in its periphery to a multi-armed water soluble polymer.

FIG. 1 provides a schematic illustration of an exemplary approach for preparing a hydrogel composition, e.g., in the form of a bead, comprising an alginate matrix covalently crosslinked in its periphery to a multi-armed water soluble polymer. An alginate polymer comprising both ionically reactive functional groups (e.g., carboxyls) and covalently reactive functional groups, B, that are selectively covalently reactive, is electrostatically crosslinked in the presence of an ionic crosslinking agent (e.g., calcium ions or other multivalent cations) to form an alginate matrix comprising ionic crosslinks. Covalently reactive functional groups, B, of the alginate matrix selectively react with functional groups, D, comprised at the termini of one or more polymer arms of a multi-armed water soluble polymer, to form covalent crosslinks in the periphery of the alginate matrix, indicated by horizontal lines. The covalent crosslinks are formed at the external surface of the ionically crosslinked alginate matrix and extend into the matrix a distance from the surface (e.g., about 100 microns, or about 10 microns or about 1 micron). For embodiments in which multiple layers are formed, excess covalent reactive groups, D, in the periphery of the hydrogel form are then reacted with functionalized alginate comprising covalent reactive groups, B, to form a hydrogel having an additional surface layer of alginate covalently crosslinked to the multi-armed water soluble polymer comprising the periphery, and so forth.

Generally, the relative amounts of reactants, degree of modification of the alginate, selection of multi-armed water soluble polymer, number of polymer arms, selection of complementary reactive groups, reaction conditions, and the like are adjusted to provide optimal covalent crosslinking on the periphery of the alginate matrix. As described above, by virtue of judiciously selecting a multi-arm water soluble polymer for covalent attachment to a derivatized alginate matrix, provided is a hydrogel composition comprising one or more of the particularly advantageous stability or other features described herein.

The covalent coupling reaction utilized to form the peripheral covalent crosslinks (by reaction of the derivatized alginate with the multi-armed water soluble polymer) is typically carried out using conventional reaction conditions known to those of skill in the art, depending upon the nature of the reacting groups and resulting linkages. The resulting hydrogel comprises covalent crosslinks where the resulting covalent linkage is a product of a first functional group of the multi-armed water soluble polymer with a second functional group of the derivatized alginate. The precise nature of the covalent crosslinks will depend on the particular reaction pairs employed. In one or more embodiments, preferred reaction pairs are those that react under mild and controllable reaction conditions (e.g., click chemistry conditions), particularly in instances in which the alginate matrix comprises living cells or other sensitive materials.

Generally, the covalent crosslinks can be formed in any of a number of suitable solvents, including for example, water, alcohol, acetonitrile, tetrahydrofuran, etc., but is typically carried out in an aqueous medium, optionally in the presence of one or more organic co-solvents. Generally an aqueous mixture comprising the derivatized alginate matrix as described above is reacted with a multi-armed water soluble polymer comprising functional groups (i.e., a first functional group) reactive with functional groups comprised within the derivatized alginate matrix (i.e., second functional groups). Typically, the covalent coupling reaction is conducted at a temperature ranging from about 0° C. to 60° C., or from about 0° C. to 50°, or from about 2° C. to 50° C., or from about 3° C. to 40° C., or within a temperature range from about 0° C. to 10° C., or from about 20° C. to 30° C., or at about 25° C. In one or more alternative embodiments, the reaction is carried out at room temperature. In some embodiments, the reaction is conducted at a temperature ranging from about 25° C. to about 37° C. (i.e., from about room temperature to body temperature). In one or more embodiments, the reaction is carried out at a temperature below room temperature, e.g., from about 0° C. to 10° C. In some embodiments, the reaction is carried out at 4° C. For embodiments in which the alginate matrix comprises encapsulated living cells, it may, in some instances, be preferable to carry out the reaction at temperatures below room temperature.

In one or more embodiments, the covalent crosslinking reaction is carried out under conditions that do not require the presence of a catalyst or a radical initiator, and which form non-toxic side products. In one or more preferred embodiments, the first and second functional groups are selectively reactive. For reactions conducted in an aqueous medium, generally the pH is in a range from about 6 to about 8, or from about 6.5 to about 7.5. In some preferred embodiments, the pH of the reaction mixture is in a range from about 7.0-7.5. The aqueous reaction medium may optionally comprise one or more buffers. Generally, the covalent crosslinking reaction is carried out for a period ranging from 1 minute to about 15 hours, depending on the reaction conditions employed, the degree of modification of the alginate matrix, the number of functional groups contained within the multi-armed water soluble polymer, the relative molar ratios of reactants, and the like. More typically, the covalent crosslinking reaction is carried out for a period of from about 5 minutes to about 2.5 hours, or from about 4 minutes to about 2 hours, or for about 15 minutes to 1.5 hours, or from about 30 minutes to an hour. Illustrative concentrations of functionalized alginate are from about 0.5 weight percent to about 25 weight percent in the reaction mixture; additional exemplary concentration ranges are from about 2 weight percent to about 20 weight percent; or from about 5 weight percent to about 18 weight percent of functionalized alginate in the reaction mixture. Illustrative amounts of the multi-armed water soluble polymer in the reaction mixture are from about 0.1 weight percent to about 50 weight percent, or from about 1 weight percent to about 40 weight percent. Depending upon the desired number of covalently crosslinked interlocked surface layers and desired degree of crosslinking, the molar ratio of the first functional group to the second functional group may range from about 1.0 to about 5; higher ratios are typically employed when covalent attachment to form additional surface layers is desired.

The degree of crosslinking in the resulting peripherally crosslinked hydrogel composition can be estimated by the degree of swelling. Exemplary hydrogel compositions will exhibit a relatively low degree of swelling, e.g., of less than about 50% by weight. Certain exemplary compositions will swell by less than about 40% by weight, or even less than about 30% by weight. Typically, degree of swelling is measured by placing the hydrogel composition in any suitable form (e.g., bead, capsule, thread, fiber, filament, etc.) in 1 mM phosphate buffered saline for a certain period of time, e.g., 1 hour, and measuring its increase in mass over a given period of time.

As described above, any suitable reaction pairs (i.e., first and second functional groups) may be employed to provide the instant hydrogel compositions, where the covalent crosslinks are the product of the reaction pair. Representative covalent crosslinking reactions include cycloadditions such as 1,2-dipolar cycloadditions and hetero-Diels alder cycloadditions; nucleophilic ring openings of strained heterocyclic electrophiles such as aziridines, epoxides, cyclic sulfates, episulfonium, etc.; non-aldol carbonyl chemistry to form ureas, thioureas, hydrozones, oxime ethers, amides and aromatic heterocycles; and additions to carbon-carbon multiple bonds, such as epoxidations, aziridinations, dihydroxylations, sulfenyl halide additions, nitrosyl additions, and Michael additions. Reaction pairs that are selectively reactive under mild conditions, relatively fast, regiospecific, form by-products that are readily removed, and that result high product yields, are preferred in some embodiments, and in particular in those embodiments in which the alginate matrix contains living cells or relatively unstable biomolecules. See, for example, Hein, et al., Pharm Res. 2008, October 25(10):2216-2230, and the exemplary reaction pairs described therein. Illustrative selective functional group pairs for covalent coupling include azide-DBCO (dibenzocyclooctyne) (resulting in a triazole linkage), thiol-norborene (Michael addition), and tetrazine-norborene (pyrazo linkage). In one or more embodiments, the covalent attachment between the alginate and the multi-armed water soluble polymer is a cycloaddition reaction between an azide and a terminal alkyne to form a 1,2,3-triazole. In some other embodiments, the covalent attachment between the alginate and the multi-armed water soluble polymer is a Diels-Alder reaction. In yet some further embodiments, the covalent attachment between the alginate and the multi-armed water soluble polymer takes place via a Michael addition. For example, reaction between a derivatized alginate and a multi-armed water soluble polymer comprising an azide-DBCO reaction pair may be carried out in a 5% aqueous solution for about 1 minute to about 5 minutes; reaction between a derivatized alginate and a multi-armed water soluble polymer comprising an azide-cyclooctyne reaction pair may be carried out at room temperature for about 1-2 hours; reaction between a derivatized alginate and a multi-armed water soluble polymer comprising an azide-electron deficient alkyne reaction pair may be carried out, for example, in water at room temperature for about 12-15 hours; reaction between a derivatized alginate and a multi-armed water soluble polymer comprising a tetrazine-alkene reaction pair suitable for carrying out a retro[4+2] cycloaddition may be carried out, for example, for about 30 minutes for 1 hour, while reaction between a derivatized alginate and a multi-armed water soluble polymer comprising a thiol-alkene reaction pair in the presence of UV light may be effected in about 30 minutes to 1 hour.

Functionalized alkynes useful for providing functionalization of either the alginate or the multi-armed water soluble polymer include, e.g., alkylene-PEG5-acid, R-3-amino-5-hexynoic acid hydrochloride, S-3-amino-5-hexynoic acid hydrochloride, R-3-(Boc-amino)-5-hexynoic acid, S-3-(Boc-amino)-5-hexynoic acid, N-Boc-4-pentyne-1-amine, Boc-propargyl-Gly-OH, 3-ethynylaniline, 4-ethynylaniline, 4-pentynyl-1-amine, propargyamine hydrochloride, propargyl chloroformate, propargyl-NHS ester, N—Z-4-pentyne-1-amine (available from Sigma Aldrich), where the functional group other than alkyne is used for introduction of the alkyne functionality into either the alginate or the multi-armed water soluble polymer. DBOC reagents include, for example, DBCO-C6 ester, DBCO-NHS ester, DVCO-PEG-4-NHS ester, DBCO-PEG-5-NHS ester, DBCO-PEG-4 amine, DBCO-amine, and similar reagents functionaled with a group suitable for introduction into either the alginate or the multi-armed polymer. The preceding DBCO reagents are available from Click Chemistry Tools (Scottsdale, AZ); their structures are incorporated herein by reference. As will be evident from the description herein, these alkyenes are meant to be illustrative but not at all limiting. Illustrative azides include, but are not limited to 4-acetamidobenzenesulfonyl azide, 1-azidoadamantane, 2-azido-4-octadecene-1,3-diol, 5-azidopentanoic acid, 3-azido-1-propanamine, and 3-azido-1-propanol (Sigma-Aldrich). Azides having short PEG linkers that may also be used for introduction of an azide moiety include O-(2-aminoethyl)-O'-(2-azidoethyl)heptaethylene glycol, O-(2-aminoethyl)-O'-(2-azidoethyl)nonaethylene glycol, 0-(2-aminoethyl)-O'-(2-azidoethyl)pentamethylene glycol, and the like (Sigma-Aldrich).

Following formation of the peripheral covalent crosslinks, sequential additional of covalently crosslinked interlocked surface layers is conducted until a hydrogel composition having the desired number of covalently crosslinked surface layers is formed. Without being bound by theory, the resulting hydrogel, when prepared by sequential addition of multiple layers, may possess an extensive innerlocked cross-linked-linked surface, in which the multi-armed polyethylene glycol penetrates into a proximate layer. Generally, the hydrogel optionally comprises from 1 to 20 additional sequential molecular surface layers of alginate covalently crosslinked to a multi-armed water soluble polymer as described above, or from about 1-10 additional sequential molecular surface layers.

Example 4 describes the preparation of an exemplary hydrogel composition comprising an alginate matrix having peripheral covalent crosslinks. The reaction is also provided schematically as FIG. 2. The covalent reaction pair utilized to provide the peripheral covalent crosslinks is azide-DBCO. Alginic acid is first derivatized to comprise reactive azide groups, e.g., by reaction of alginic acid carboxyl groups with an azide-functionalized linker such as 3-azido-aminopropane. The azide-functionalized alginate is electrostatically crosslinked to provide an alginate matrix; the azide-functionalized alginate matrix is then reacted with 4-arm polyethylene glycol-DBCO (dibenzylcyclooctyne), "4-arm PEG-DBCO", under mild reaction conditions, e.g., in deionized water, to provide alginate beads having peripheral covalent triazole-containing crosslinks. The degree of covalent crosslinking can be modified by adjustment of the degree of functionalization of the alginate, the number of polymer arms in the multi-armed polymer, and the ratio of the reacting functional groups (e.g., azide to DBCO). Additional surface layers may be covalently attached by further, sequential reactions with azide-functionalized alginate, followed by multi-arm water soluble polymer, until a desired number of covalently crosslinked surface layers is formed.

The hydrogel composition may optionally further comprise a biocompatible surface layer on its outermost surface, where the biocompatible surface layer is other than the alginate or the multi-armed water soluble polymer. The biocompatible surface layer is preferably but is not necessarily covalently attached to the hydrogel composition. In instances in which the biocompatible polymer is covalently attached to the hydrogel composition, the biocompatible polymer will comprise a functional group suitable for attachment to an outer later of the hydrogel composition, i.e., in some embodiments, to an alginate layer or, in other embodiments, to a multi-armed water soluble polymer layer. For example, the biocompatible polymer may DBCO-functionalized for reaction with azide groups present on the outer surface of the hydrogel composition. Alternative, the biocompatible polymer may be azide-functionalized for reaction with DBCO groups on the outer layer of the hydrogel composition. The selection of a group suitable for covalent attachment to the outer surface of the hydrogel will be apparent to one skilled in the art. Exemplary reaction group pairs suitable for such coupling are described herein.

Illustrative biocompatible polymers suitable for forming a biocompatible surface layer, if present, include, for example, polyethylene glycol, phosphocholine-containing polymers and copolymers (Ishihara, K., et al., *Polymer Journal* 22(5), (1990), 355-360; Xu, Y, et al., *Biomaterials,* 31 (2010) 8839-8846; Yu, X., et al., *Nature Materials,* 11 (2012) 468-476; Shiino, D., et al., U.S. Pat. No. 6,214,957), poly (vinyl alcohol), carboxymethylcellulose, chitosan, hydroxyapatite, dextran, hydroxyethylstarch, gelatin, collagen, elastin, fibronectin, pronectin, laminin, and hyaluronic acid. In some embodiments, the biocompatible surface layer comprises a biocompatible homo-polymer or copolymer functionalized to comprise pendant phosphocholine groups. In some preferred embodiments, the biocompatible polymer used to provide a biocompatible surface layer comprises functional groups suitable for covalent attachment to the outermost surface of the hydrogel composition. The functional group(s) may be directly attached to the biocompatible polymer or may be introduced via a short intervening linker such as a short PEG chain, a carboxymethyl group, an amino acid or oligopeptide linker, or any other suitable linking group. Such linking groups will typically contain from about 2 to about 20 atoms, or from about 2 atoms to about 15 atoms, or from about 2 to 10 atoms. Example 8 describes the use of a short PEG linker having 4 monomer repeat units. Illustrative functional groups have been described previously herein, and are selective for reaction with functional groups contained within the outermost surface of the hydrogel composition. Illustrative reaction pairs are click chemistry reaction pairs. The synthesis of an exemplary polymer comprising phosphocholine and lysine groups as well as a click chemistry functional group suitable to provide a biocompatible surface coating on an alginate hydrogel by covalent attachment thereto (PC-Lys-MA-DBCO) is described in Example 8.

More particularly, Example 8 describes the synthesis of illustrative biocompatible methacrylamide polymers comprising phosphocholine and L-lysine functional groups. A preferred biocompatible polymer comprises the following monomeric units,

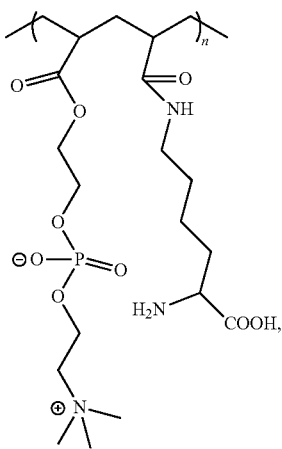

wherein from about 5 mole % to about 100 mole % of the lysine moieties (e.g., 5, 10, 15, 20, 25, 30, 35, 40, 45, 50, 55, 60, 65, 70, 75, 80, 85, 90, 95 or 100 mole %) in the polymer possess a click chemistry functional group such as DBCO, or any other click chemistry-related functional group, covalently attached either directly or via a short linker as described above, to either the lyine amino or carboxyl groups. Illustrative linkers include short PEG-mers having from about 3-5 ethylene oxide repeat units, or dicarboxylic acids having a carboxy function at each terminus and an intervening short alkylene chain, $\sim(CH_2)_n\sim$, where n ranges from about 3 to 6. The PC-LY-MA-CLICK polymer will generally possess a weight average molecular weight in a range from about 10 kD to about 1 million kD, preferably in a range from about 25 kD to about 500 kD.

The biocompatible polymers modified to contain click-reactive functional groups were prepared by polymerizing the illustrative monomers, methacrylamide phosphocholine and N-methacrylamide L-lysine, in an aqueous system with water soluble azo-initiators at an elevated temperature. The solubility of the resulting polymers in an aqueous system can be tailored by adjusting the mole ratio of phosphocholine to lysine-containing monomers. As the mole percentage of the lysine-containing monomer is increased, the solubility of the resultant copolymer decreases. Preferred mole percentages of lysine in a phosphocholine-lysine copolymer such as described in Examples 8 and 9 are in a range of about 1 mol % to about 30%, or are preferably in a range of about 5 mol % to about 20 mol %, to provide a water-soluble polymer, e.g., for providing a biocompatible surface layer for a hydrogel composition as provided herein.

Features of the Hydrogel Composition

The instant hydrogels possess several desirable features, including notable stability under stress conditions (e.g., 40° C. and 1 mM phosphate buffered saline) for an extended period of time. In one or more embodiments, the instant compositions not only maintain their shape and gel integrity (i.e., have good mechanical stability), but also retain their semi-permeability and other rheological properties for an extended period of time when placed under high stress conditions modelling an in vivo environment. More specifically, the alginate hydrogel composition described herein are stable and maintain their shape and integrity for up to at least 30 days, e.g., up to at least 45 days, or up to at least 60 days, and even up to at least 90 days, when stored in 1 mM PBS at 40° C. See, for example, Examples 6 and 7, describing permeability and mechanical stability features of the instant hydrogel compositions. In one or more embodiments, the instant hydrogels additionally maintain their semi-permeability under simulated in vivo conditions for an extended period of time, i.e., for at least 30 days, for up to at least 45 days, for up to at least 60 days, and indeed up to 3 months (at least 90 days)—making them surprisingly structurally and functionally resilient. By virtue of the foregoing, the instant materials are advantageously suited for use in therapeutic products, and in particular, for delivering viable cells, among other uses.

The permeability studies described in Example 6 demonstrate the semi-permeable nature of exemplary surface cross-linked alginate hydrogel compositions throughout the course of a 90-day stability study at 40° C. in 1 mM PBS. More specifically, while the hydrogel composition (having from 1-7 covalently crosslinked surface layers) was permeable to low molecular weight fluorescent-labeled dextran of about 10 kDa size (FITC-dextran 10K), as indicated by the observation of intense fluorescence within the bead), the higher molecular weight species, e.g., FITC-dextran 70 kDa, 150 kDa and 250 kDa, were excluded, as indicated by an absence of fluorescence detected within the bead. Similarly, the bead (having from 1-7 covalently crosslinked surface layers) was impermeable to the antibody, IgG (molecular weight of approximately 150 kDa). This illustrates the stability and durability of the semi-permeable nature of the hydrogel compositions at body temperature in 1 mM PBS. Notably, semi-permeability was stable under the simulated in vivo conditions for an extended period of time, i.e., at least 3 months, and semi-permeable nature of the beads was observed for beads having a single covalently crosslinked surface layer in its periphery, as well as for those having multiple covalently crosslinked surface layers.

The actual molecular weight cut-off for molecular species capable of permeating the hydrogel composition may vary depending upon the particulars of the hydrogel composition and can be tailored for a desired use or application. For example, the composition may, in one or more embodiments, be permeable to molecular species having a molecular weight of about 100 kDa or less, or of about 75 kDa or less, or of about 50 kDa or less, or of about 25 kDa or less, or of about 20 kDa or less, or of about 10 kDa or less and correspondingly, be impermeable to larger molecular species than each of the foregoing, respectively.

The compressive strength of different types of alginate hydrogel beads following incubation under various stress conditions is described in Example 7. The alginate-poly-L-ornithine alginate (APA) beads, which are a stabilized bead of the prior art, exhibit a high cohesive strength in water at room temperature (designated composition "ITL-A"), however, upon increasing the stringency of the incubation conditions, e.g., to incubation in 1 mM PBS, at 40° C., a notable loss in cohesive strength is observed ("ITL-B"), especially at axial force values above 1N. In contrast, the AlgAz-PEGD beads (both single layer and 7-layer), which are exemplary of the hydrogels that are covalently crosslinked in the periphery described herein, exhibit essentially no significant loss of strength upon increasing the stringency of the incubation conditions. Interestingly, the single layer material appears to maintain its strength under stress conditions to the same degree as the 7-layer material. The 7-layer material further maintained its cohesive strength for an extended time period in 1 mM PBS and 40° C., further demonstrating the advantageous nature of these exemplary alginate materials.

Figure 4:
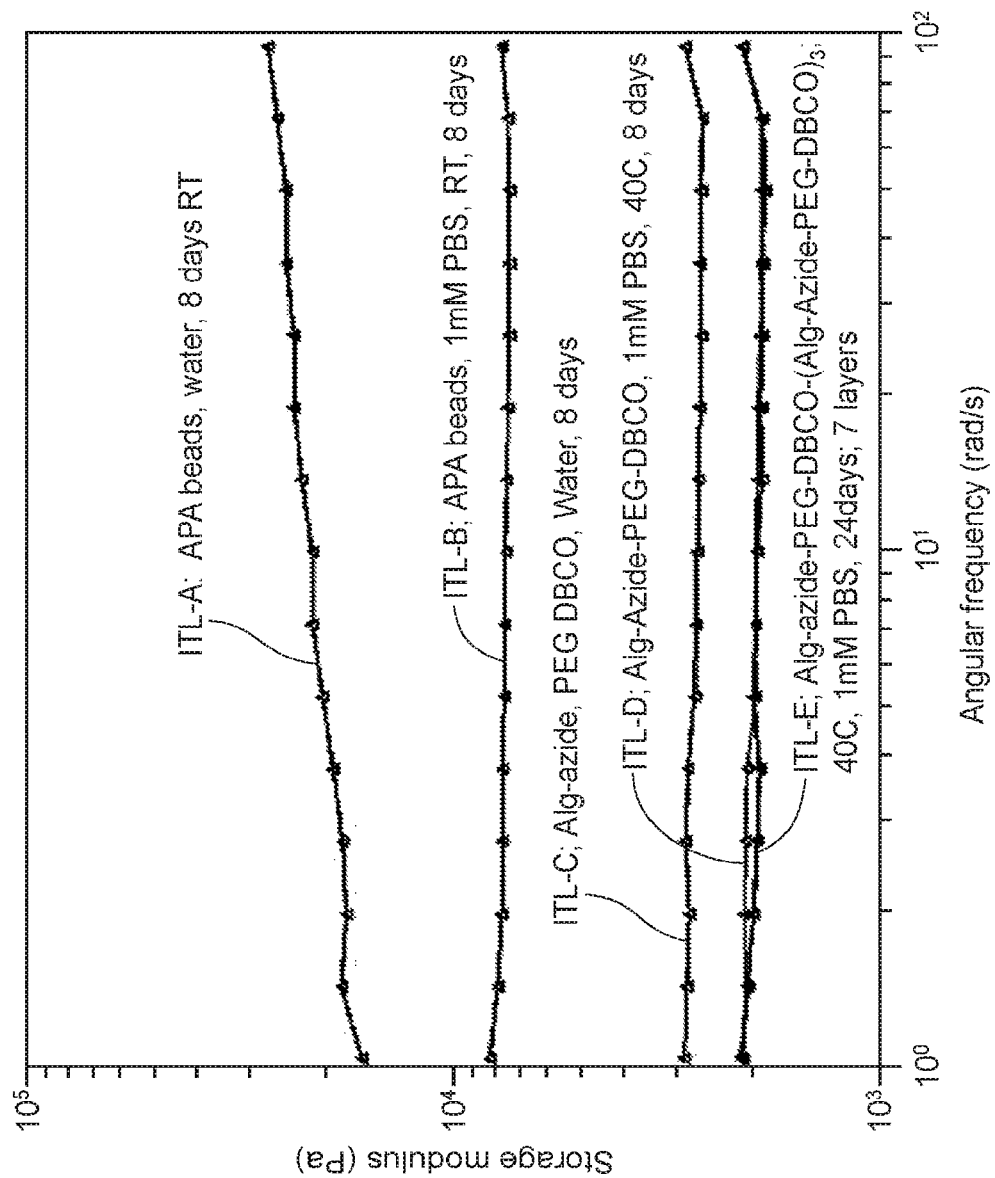
FIG. 4 illustrates the storage modulus (E') in Pa versus angular frequency in rad/s for different alginate beads following incubation under specified conditions as described in Example 7.

The storage modulus, which measures the elastic response of a material (its ability to store mechanical energy), was determined for illustrative alginates as illustrated in FIG. 4. As shown in FIG. 4, the APA ionically crosslinked beads exhibit a much higher storage modulus than the covalently crosslinked Alg-Az-PEGD beads (one covalently cross-linked layer in the periphery of the alginate matrix), under both sets of incubation conditions. The storage modulus of the single layer and the 7-layer AlgAz-PEGD beads was essentially the same under the 1 mM PBS/40° C. stringency conditions, regardless of time of incubation.

Figure 5:
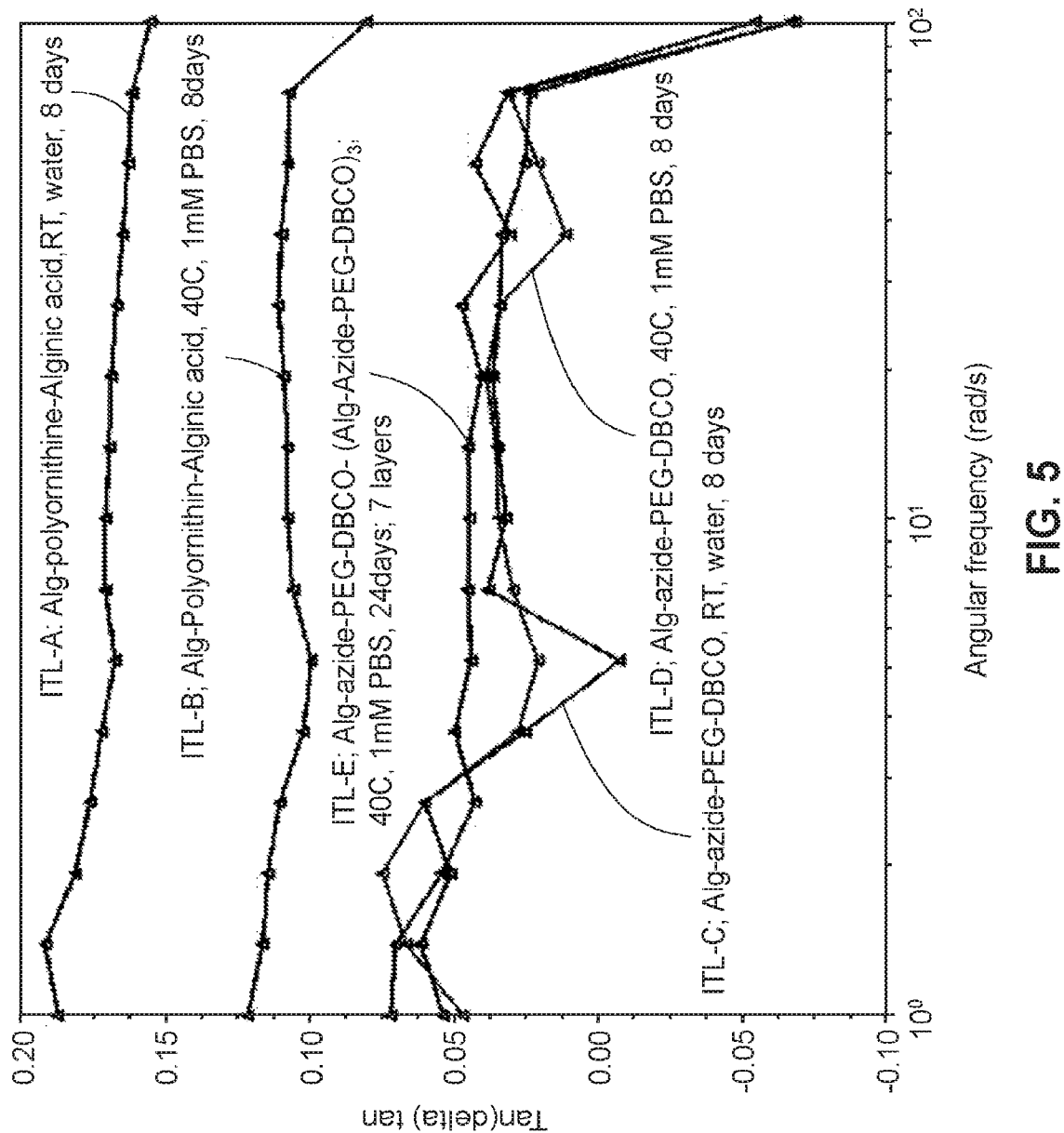
FIG. 5 illustrates the tan delta values (E"/E') versus angular frequency (rad/s) of different alginate beads (ionically crosslinked and covalently crosslinked on their surface) following incubation under specified conditions as described in Example 7.
Figure 6:
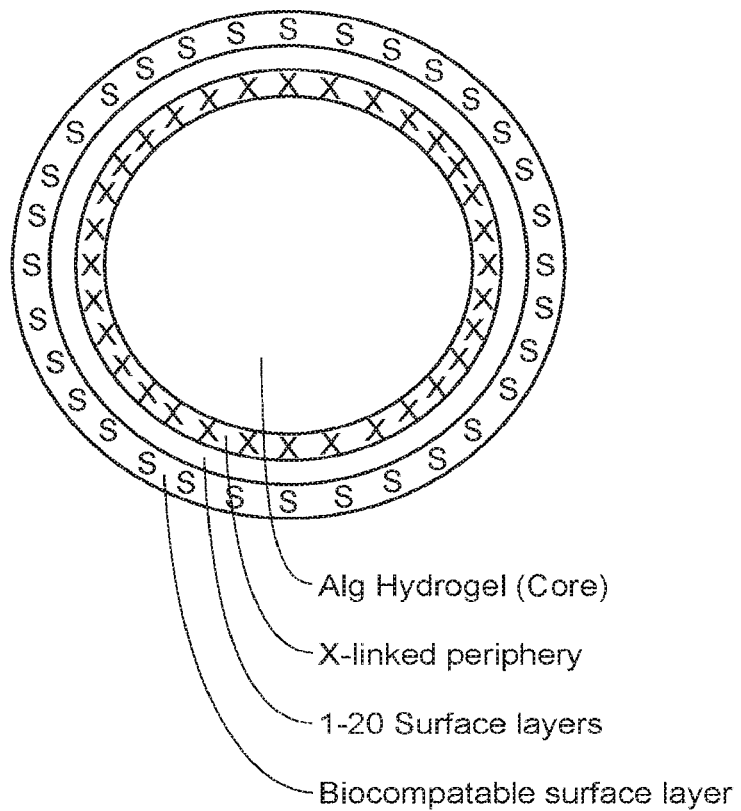
FIG. 6 is a schematic representation of an exemplary semi-permeable hydrogel bead comprising an ionically crosslinked alginate matrix (i.e., core, innermost portion of hydrogel) that is covalently crosslinked in its periphery (indicated by "X"s) to a multi-arm water soluble polymer. The bead (or other suitable hydrogel form) may further comprise from 1-20 additional covalently crosslinked surface layers of alginate covalently crosslinked to a multi-armed water soluble polymer (next outermost layer(s) adjacent to periphery indicated by "X"s), and may optionally contain an outermost biocompatible surface layer (layer indicated by "B"s).

Tan delta (E"E'), where E" is storage modulus and E' is loss modulus, was determined for the illustrative alginates shown in FIG. 5. Tan delta provides a measure of the energy dissipation of a material. As shown in FIG. 5, the tan delta is notably higher for the APA ionically crosslinked beads in comparison to the Alg-Az-PEGD beads. The higher tan delta of the APA materials is indicative of their instability, as these materials dissipate energy more effectively. This may be attributed to the relatively higher order of molecular motion of the APA materials when compared to the Alg-Az-PEGD beads. In contrast, the Alg-Az-PEGD beads exhibit a much lower tan delta than the APA-materials across the range of angular frequencies measured, indicating that these illustrative materials exhibit a limited dissipation of energy. From this, it may be deduced that these exemplary materials possess a more highly structured, and therefore stable polymer framework, with less molecular motion. The tan delta values for the single layer and 7-layer Alg-Az-PEGD beads are quite similar, as can be seen in the three bottom plots in FIG. 6.

In one or more embodiments, the hydrogel composition possesses a tan delta below about 0.10, i.e., less than 0.09, 0.08, 0.07, 0.06, 0.05, 0.04, 0.03, e.g., about 0.04 or about 0.03. In some embodiments, the hydrogel composition is characterized by a first tan delta value determined at the time the composition is subjected to storage at 40° C. in 1 mM phosphate buffered saline (day 0), and a second tan delta value determined after the composition has been stored for 30 days at 40° C. in 1 mM phosphate buffered saline, wherein the first tan delta value and the second tan delta value are the same or differ by no more than about 0.05. In yet some additional embodiments, the first tan delta value and the second tan delta value differ by no more than about 0.04, or by no more than about 0.03, or by no more than about 0.01, when evaluated under the conditions described above.

The instant hydrogels may take any of a number of forms. Illustrative hydrogel forms include, for example, a bead, capsule, sheet, membrane, thread, fiber, filament, particle, sponge, mesh, foam, scaffold and composites of any of the foregoing.

The hydrogel compositions are suitable for use in biomedical applications, for example, for immunoisolation of cells, drug delivery, coatings, and the like. The compositions may also be used be used for any suitable purpose, e.g., for embryonic development, tissue organization (e.g., as a scaffold), wound healing (e.g., as a wound filler), angiogenesis and tumorigenesis, and may be comprised in a macro- or in a microdevice. The compositions are particularly useful as devices for the implantation of cells, for example for implantation of pancreatic cells (e.g., islet cells) to treat a subject with diabetes. For immunoisolation of cells, cells can be obtained directly from a donor, from culture of cells from a donor, or from established cell culture lines. In some embodiments, cells are obtained directly from a donor, washed and incorporated into the hydrogel composition. The cells can be cultured (e.g., differentiated and/or expanded) using any suitable culture techniques known to those skilled in the art of tissue culture prior to incorporation into the hydrogel composition. In a preferred embodiment, the cells are autologous—i.e., derived from the individual into which the cells are to be transplanted, but may, in one or more alternative embodiments, be allogeneic or xenogeneic. For example, islet cells of the pancreas may be incorporated into the hydrogel compositions and implanted to achieve glucose regulation by appropriate secretion of insulin to treat diabetes. Cells from other endocrine tissues can also be implanted. The instant hydrogels can be used to provide multiple cell types, including genetically altered cells, e.g., within a three-dimensional scaffolding, for the efficient transfer of large number of cells and the promotion of transplant engraftment for the purpose of creating a new tissue or tissue equivalent. The hydrogel compositions can also be used for immunoprotection of cell transplants while a new tissue or tissue equivalent is growing by excluding the host immune system. The instant hydrogel formulations may, in certain embodiments, upon implantation in a subject, elicit either no immune response or a minimal immune-response. In one or more embodiments, the instant hydrogel compositions, upon implantation, will result in one or more of the following: minimal fibrosis, i.e., minimal fibrous deposition, minimal or reduced nutrient isolation, and donor tissue necrosis.

The hydrogel compositions can be combined with humoral factors to promote cell transplantation and engraftment. For example, the hydrogel compositions can be combined with angiogenic factors, antibiotics, antiinflammatories, growth factors, compounds which induce differentiation, and other factors which are known to those skilled in the art of cell culture.

The instant hydrogels can be used for delivery of many different cell types to achieve different tissue structures. In one or more embodiments, a hydrogel composition that contains a desired type of cell can be injected directly into a site where it is desired to implant the cells. The hydrogel may also be molded and implanted in one or more different areas of the body to suit a particular application.

The hydrogel compositions may also be used as drug delivery vehicles, for example, to locally delivery a bioactive agent topically, intramuscularly, intra-articularly, subcutaneously, to the ocular region, intradermally, to treat in-bone defects, in cartilage defects, in tissue voids, and to in-body lumens.

The instant hydrogel compositions will now be described in connection with certain embodiments, which are not intended to be limiting in scope. On the contrary, the present application covers all alternatives, modifications, and equivalents as included within the scope of the claims. Thus, the following is for the purposes of illustration of certain embodiments.

EXAMPLES

The following examples are put forth to provide those of ordinary skill in the art with a complete disclosure and description of how the compositions, hydrogels, and methods provided herein are made and evaluated, and are intended to be purely exemplary. Thus, the examples are in no way intended to limit the scope of what the inventors regard as their invention. There are numerous variations and combinations of reaction conditions, e.g., component concentrations, desired solvents, solvent mixtures, temperatures, pressures, and other reaction parameters and conditions that may be employed to optimize product characteristics such as stability, purity, mechanical properties, yield, and the like. Such are considered as well within the scope of the present disclosure.

Materials

Alginic acid from algae, 200 kD 4-arm polyethylene glycol carboxylic acid, 5 and 10 kD (pentaerythritol core)

DBCO-amine (dibenzylcyclooctyne amine),

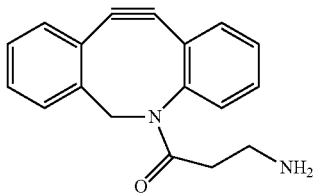 [SMILES: NCCC(=O)N1Cc2ccccc2C#Cc2ccccc21]

EDCI: 1-ethyl-3-(3-dimethylaminopropyl)carbodiimide (additional synonyms include EDC)

MES: 2-(N-morpholino)ethanesulfonic acid

NHS: N-hydroxysuccinimide

DCM: dichloromethane

DI water: deionized water

PBS: phosphate buffered saline

FITC: fluorescein isothiocyanate

Example 1

Modification of Alginic Acid with 3-Azido-Aminopropane

The carboxyl groups of alginic acid were randomly modified with different amounts of 3-azido-aminopropane to provide aliginic acid having differing degrees of azide substitution. The alginic acid azide polymer was purified by dialysis. Chemically modified alginic acid azide having azide mole equivalents of 5%, 10%, 15% and 20% were prepared as follows.

1A. Modification of Alginic Acid with 0.2 Equivalents of 3-Azido-Aminopropane (20% Substitution)

Alginic acid (1 g, 5.05 mM) was dissolved in MES (2-(N-morpholino)ethanesulfonic acid) (0.1 M) and NaCl (0.3 M) buffer at pH 6.5 to provide a solution having a 0.5% concentration of alginic acid. 3-azido-1-propamine (0.2 eq., 101.06 mg), EDC.HCl (1 eq., 967.5 mg) and NHS (0.4 eq., 232.34 mg) were added, and the reaction mixture was stirred for 24 hours at room temperature. The reaction mixture was then dialyzed against deionized water using a decreasing salt gradient from 150 mm to 0 mm. After dialysis, the product was lyophilized and stored at 4-8° C.

1B. Modification of Alginic Acid with 0.15 Equivalents of 3-Azido-Aminopropane (15% Substitution)

Alginic acid (1 g, 5.05 mM) was dissolved in MES (0.1 M) and NaCl (0.3 M) buffer at pH 6.5 to provide a solution having a 0.5% concentration of alginic acid. 3-azido-1-propamine (0.15 eq., 75.79 mg), EDC·HCl (0.75 eq., 725.62 mg) and NHS (0.3 eq., 174.26 mg) were added and the reaction mixture was stirred for 24 hours at room temperature. The reaction mixture was then dialyzed to against deionized water using a decreasing salt gradient from 150 mm to 0 mm. After dialysis, the product was lyophilized and stored at 4-8° C.

1C. Modification of Alginic Acid with 0.10 Equivalents of 3-Azido-Aminopropane (10% Substitution)

Alginic acid (1 g, 5.05 mM) was dissolved in MES (0.1 M) and NaCl (0.3 M) buffer at ph 6.5 to provide a solution having a 0.5% concentration of alginic acid. 3-azido-1-propamine (0.1 eq., 50.53 mg), EDC·HCl (0.5 eq., 483.75 mg) and NHS (0.2 eq., 116.17 mg) were added and the reaction mixture was stirred for 24 hours at room temperature. The reaction mixture was then dialyzed against deionized water using a decreasing salt gradient from 150 mm to 0 mm. After dialysis, the product was lyophilized and stored at 4-8° C.

1D. Modification of Alginic Acid with 0.05 Equivalents of 3-Azido-Aminopropane (5% substitution)

Alginic acid (1 g, 5.05 mM) was dissolved in MES (0.1 M) and NaCl (0.3 M) buffer at ph 6.5 to provide a solution having a 0.5% concentration of alginic acid. 3-azido-1-propamine (0.05 eq., 25.26 mg), EDC·HCl (0.25 eq., 241.87 mg) and NHS (0.1 eq., 58.09 mg) were added and the reaction mixture was stirred for 24 hours at room temperature. The reaction mixture was then dialyzed against deionized water using a decreasing salt gradient from 150 mm to 0 mm. After dialysis, the product was lyophilized and stored at 4-8° C.

Example 2

Synthesis of 4-Arm PEG-DBCO 4-arm PEG having carboxylic acid groups at each of its four termini, "4-Arm PEG-COOH", 10 kD (1 gm) was dissolved in 40 ml of dichloromethane (DCM). EDC·HCl (5 eq., 766.8 mg), NHS (2 eq., 184.14 mg) and triethyl amine (5 eq., 557 l) were added to the 4-Arm PEG-COOH/DCM solution with stirring. Dibenzylcyclooctyne amine (1.05 eq., 232.12 mg) was then added, and the reaction mixture was allowed to stir at room temperature for 24 hours. Dichloromethane was removed by evaporation, and the DBCO-functionalized product was purified by column chromatography using a Sephadex g-15 column and ethanol as the eluent to provide 4-Arm PEG-DBCO.

Example 3

Preparation of Alginic Acid-Azide Beads

An aqueous solution of alginic acid azide polymer (1.5 weight %, 1.5 g per 100 mL, 20% azide-modified), as described in Example 1, was added dropwise into a 0.1M solution of $CaCl_2$ using an automated pump with a syringe fitted with a 25 gauge needle. The resulting beads were collected and washed with water.

Control: A 5 ml aqueous solution of alginic acid (1.5 wt %) was added dropwise through a 25 gauge needle to a $CaCl_2$ bath (0.1M) using an automated pump at the rate of 120 mL/minute with stirring. The resultant beads were allowed to remain in the bath for 10 minutes. The $CaCl_2$ solution was then decanted and the beads were washed three times with 50 ml water.

Stability Characterization: The alginic acid azide beads were unstable in PBS buffer. A small sample of the beads was stored in PBS at 40° C. for 24 hours. Over the 24 hour time course, the beads lost their shape and ultimately collapsed. No individual beads were visible at 24 hours.

Similar results were observed for the alginate beads (control, non-azide modified).

Behavior of the beads in PBS at 40° C. is illustrative of their behavior in vivo; that is to say, conventional ionically crosslinked alginate beads are unsuitable for delivery of active agents, cells, or the like, in vivo, due to their structural instability and collapse under physiological conditions.

Example 4

Covalent Surface Modification of Alginic Acid-Azide Beads with 4-Arm PEG-DBCO

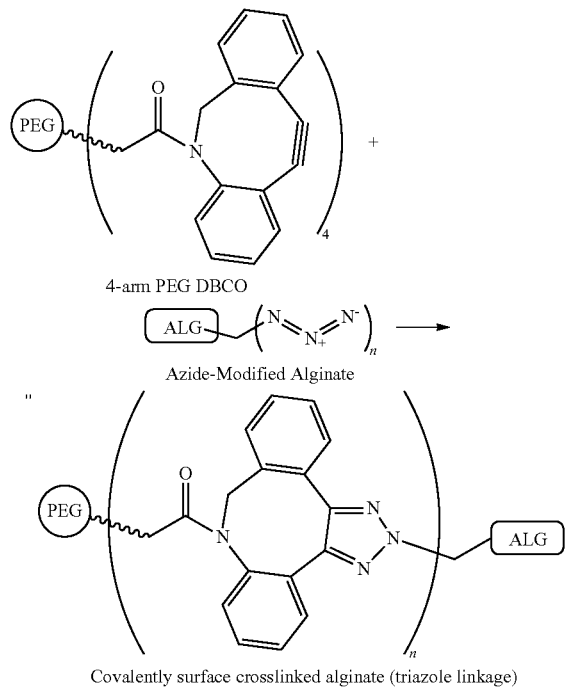

4-arm PEG DBCO

Azide-Modified Alginate

Covalently surface crosslinked alginate (triazole linkage)

Following decantation of the wash solution of the ionically crosslinked alginate azide beads from Example 3, an aqueous solution of 4-Arm PEG-DBCO prepared as described in Example 2 (200 mg in 20 mL DI water) was added to the beads, and the mixture was stirred for 30 minutes. The 4-Arm PEG-DBCO solution was then decanted, and the beads having a single covalently crosslinked interpenetrating surface layer of 4-arm polyethylene glycol attached to the alginate via 8,9-dihydro-2H-dibenzo[b,f][1,2,3]triazolo[4,5-d]azocine groups ("AlgAz-PEGD") were washed with 3×50 ml water. The beads were then stored in either buffer or water for further characterization, including shape retention, permeability, and viscoelasticity. A simplified schematic representation of the reaction is shown above and in FIG. 2.

The beads were incubated in 1 mM PBS solution at 40° C. Periodically, the beads were analyzed for size, shape, permeability, and mechanical properties.

Figure 3A:
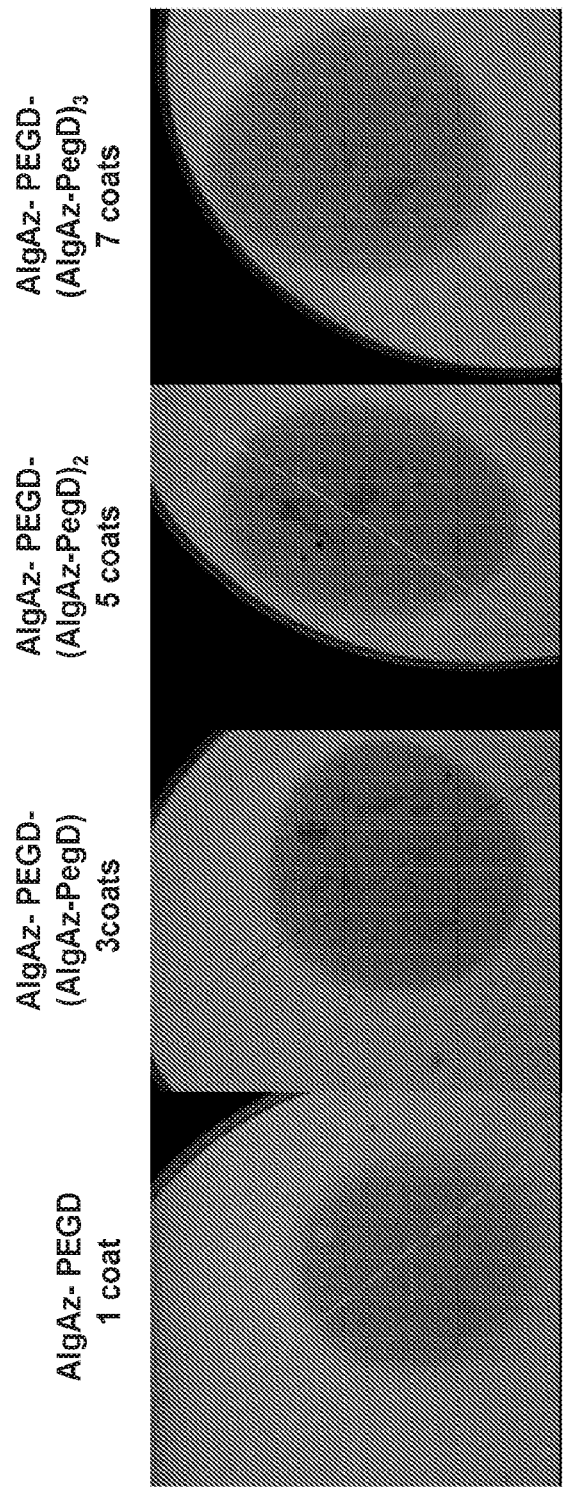
FIGS. 3A and 3B illustrate the semi-permeable nature of exemplary alginate beads having from 1 to 7 covalently crosslinked, inter-penetrating layers of a water soluble polymer as described in Example 6.
Figure 3B:
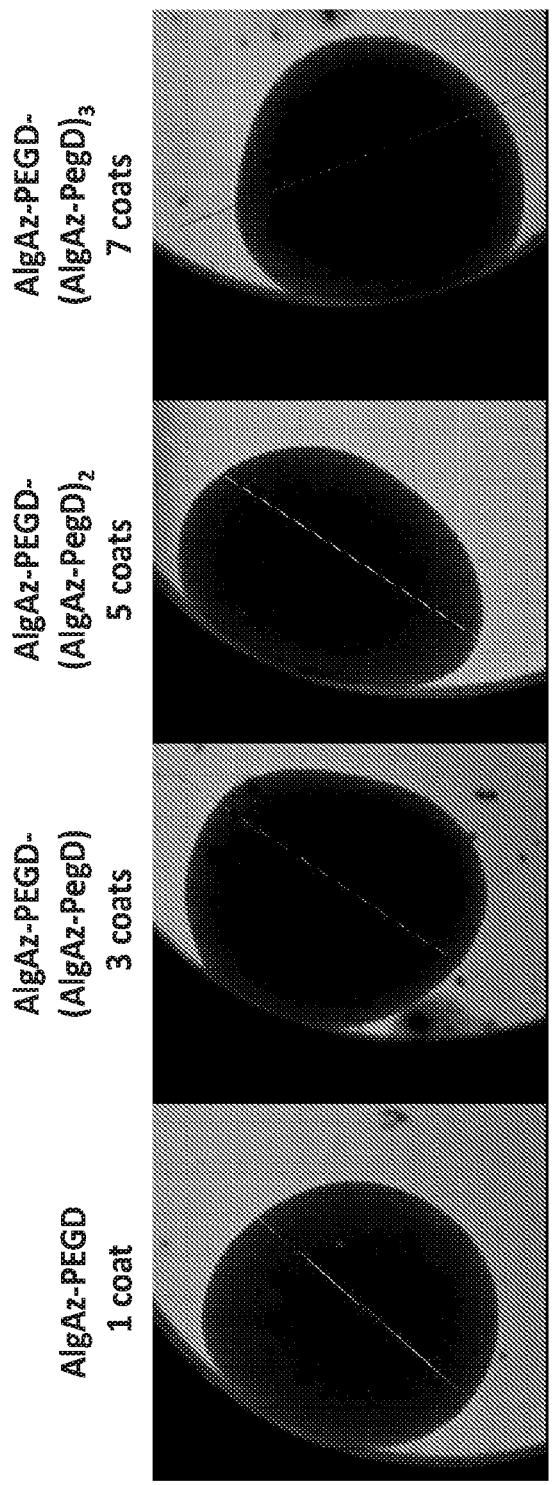

Based upon visual inspection following incubation at 40° C. in PBS, the covalently surface modified beads surprisingly retained their bead shape and maintained gel integrity for 24 hours, and beyond. Thus, in contrast to both the alginate beads and the alginate-azide modified beads without covalent crosslinking, which collapsed under storage conditions (PBS/40° C.) over the 24 hour time frame, the exemplary covalently surface-modified alginate beads exhibited superior robustness under the same conditions. Moreover, the covalently surface-modified beads (having, e.g., from 1 to 7 covalently linked interpenetrating surface layers, to be described below) maintained their bead shape and integrity for up to at least 90 days when stored in 1 mM PBS at 40° C. See FIGS. 3A-3B which demonstrate maintenance of the structural integrity of the beads. The beads were stored in deionized water at 2-8° C. for further characterization.

Example 5

Preparation of Alginic Acid-Azide Beads Having Multiple-Covalently Crosslinked Polymeric Surface Layers The surface modified heads from Example 4 having a single covalently crosslinked interpenetrating surface layer of 4-arm polyethylene glycol ("AlgAz-PEGD") were further modified by sequentially adding additional surface layers as described in Example 4, and adjusting the molar ratios of the reacting functional groups accordingly, depending upon the desired number of layers. Beads having 3, 5, and 7 covalently crosslinked surface layers were prepared as follows.

Single covalently crosslinked interpenetrating beads as described in Example 4 were added to a 20 mL 0.15 wt % solution of 20% azide-modified alginic acid and allowed to react for 30 minutes. The alginic acid solution was then decanted and the heads were washed with 3×50 mL of water. The beads were added to an aqueous solution of 4-Arm PEG-DBCO prepared as described in Example 2 (200 mg in 20 mL DI water) and the mixture was stirred for 30 minutes. The 4-Arm PEG-DBCO solution was then decanted and the beads were washed with 3×50 mL of water. The 3-layered beads were then used for further coating or stored in either buffer or water for further characterization, including shape retention, permeability, and viscoelasticity.

The above sequence was repeated to form the 5- and 7-layered beads.

Alginate beads having 3 covalently crosslinked interpenetrating surface layers are designated AlgAz-PEGD/AlgAz/PEGD, where the first layer is formed by reaction of the azide-functionalized alginate with 4-arm PEG DBCO, the second layer is formed by reaction of excess DBCO groups on the surface of AlgAz-PEGD with azide-modified alginate as described in Example 1 to form AlgAz-PEGD/AlgAz (having 2 covalently crosslinked surface layers), where excess azide reactive groups of AlgAz-PEGD/AlgAz are then reacted with 4-arm PEG DBCO to form the 3 layer hydrogel bead, AlgAz-PEGD/AlgAz/PEGD also referred to herein as AlgAz-PEGD-3. Alginate beads having 5 covalently crosslinked interpenetrating surface layers are referred to as AlgAz-PEGD(AlgAz/PEGD)$_2$ or AlgAz-PEGD-5, and alginate beads having 7 covalently crosslinked interpenetrating surface layers are referred to herein as AlgAz-PEGD(AlgAz/PEGD)$_3$ or AlgAz-PEGD-7, and so forth.

Example 6

Permeability Studies

Permeability studies were conducted using the covalently surface crosslinked modified beads from Examples 4 and 5 (having 1, 3, 5, and 7 covalently crosslinked surface layer(s)). The fluorescent molecular weight markers used in the permeability studies were dextran-FITC 10 kD, 70 kD, 150 kD, and 250 kD, bovine serum albumin FITC (BSA FITC) and immunoglobulin G-FITC (TgG FITC). The molecular weight markers were dissolved in saline at concentrations in a range of 0.1-0.2 mg/ml. The beads were incubated with the 200 μL FITC solutions in 96 well plates at 40° C./1 mM PBS for up to 90 days. Diffusion of the probes into the beads was monitored by confocal microscopy at varying time points (18 days, 67 days, 90 days).

The permeability studies demonstrate the semi-permeable nature of the exemplary surface crosslinked alginate beads throughout the course of the 90-day stability study at 40° C. in 1 mM PBS. More specifically, while the bead (having from 1-7 covalently crosslinked surface layers) was permeable to low molecular weight fluorescent-labeled dextran (FITC-dextran 10K), as indicated by the observation of intense fluorescence within the bead), the higher molecular weight species, e.g., FITC-dextran 70 kD, 150 kD and 250 kD, were impermeable, as indicated by an absence of fluorescence detected within the bead (having from 1-7 covalently crosslinked surface layers). Similarly, the bead (having from 1-7 covalently crosslinked surface layers) was impermeable to the antibody, IgG (molecular weight of approximately 150 kDa). This illustrates, for the exemplary beads described, their semi-permeable nature at body temperature in 1 mM PBS. Moreover, the beads maintained their semi-permeability under the simulated in-vivo conditions for an extended period of time, i.e., for 3 months. The semi-permeable nature of the beads was observed for beads having a single covalently crosslinked surface layer, as well as for those having multiple covalently crosslinked surface layers. Thus, based on at least the foregoing, these exemplary materials are advantageously suited for use in therapeutic products, and in particular, for providing a viable cell therapeutic product, among other uses.

Example 7

Mechanical Stability

Mechanical properties of the beads were analyzed using an RSA-G2 solids analyzer (TA Instruments) at 21° C. using parallel plate geometry (plate diameter 8 mm and gap 2 mm). A normal axial force of 0.05 n was applied and the diameter of the bead was determined by the axial position reading of the analyzer. The beads were analyzed in compression mode by applying a dynamic strain of 5% and a frequency sweep from 1 to 100 rads/s.

The compressive strength of different alginate beads following incubation under various stress conditions was determined. The following materials were evaluated:

TABLE 1

| Alginate Designation | Material and Incubation Conditions |
|---|---|
| ITL-A | Alginate-poly-L-ornithine-alginate (APA) ionically linked beads (Sigma-Aldrich)*, in water at room temperature for 8 days |
| ITL-B | Alginate-poly-L-ornithine-alginate (APA) ionically linked beads, in 1 mM PBS at 40° C. for 8 days |
| ITL-C | AlgAz-PEGD in water at room temperature for 8 days |
| ITL-D | AlgAz-PEGD in 1 mM PBS at 40° C. for 8 days |
| ITL-E | AlgAz-PEGD-7 in 1 mM PBS for 24 days |

*Leung, A., et al., *J. Microencapsul.* 2008 Sep. 25(6), 387-98.

Ionically crosslinked alginate beads as described in Example 3 were not used in the comparison due to their instability.

The APA beads exhibit a high cohesive strength in water at room temperature (ITL-A), however, upon increasing the stringency of the incubation conditions, e.g., to incubation in 1 mM PBS, at 40° C., a notable loss in cohesive strength was observed (ITL-B), especially at axial force values above 1N. In contrast, the AlgAz-PEGD beads (both single layer and 7-layer) exhibited essentially no significant loss of strength upon increasing the stringency of the incubation conditions. Interestingly, the single layer material appears to maintain its strength under stress conditions to the same degree as the 7-layer material. The 7-layer material further maintained its cohesive strength for an extended time period in 1 mM PBS and 40° C., further demonstrating the superior nature of these exemplary alginate materials.

The storage modulus, which measures the elastic response of a material (its ability to store mechanical energy), was determined for the illustrative alginates described in Table 1, as illustrated in FIG. 4. As shown in FIG. 4, the APA ionically crosslinked beads exhibited a much higher storage modulus than the covalently surface crosslinked Alg-Az-PEGD beads, under both sets of incubation conditions. The storage modulus of the single layer and the 7-layer AlgAz-PEGD beads was essentially the same under the 1 mM PBS/40° C. stringency conditions, regardless of time of incubation.

Tan delta (E"/E'), where E" is storage modulus and E' is loss modulus, was determined for the illustrative alginates described in Table 1, as illustrated in FIG. 5. Tan delta provides a measure of the energy dissipation of a material. As shown in FIG. 5, the tan delta is notably higher for the APA ionically crosslinked beads in comparison to the Alg-Az-PEGD beads. The higher tan delta of the APA materials is indicative of their instability, as these materials dissipate energy more effectively. This may be attributed to the relatively higher order of molecular motion of the APA materials when compared to the Alg-Az-PEGD beads. In contrast, the Alg-Az-PEGD beads exhibit a much lower tan delta than the APA-materials across the range of angular frequencies measured, indicating that these illustrative materials exhibit a limited dissipation of energy. From this, it may be deduced that these materials possess a more highly structured, and therefore stable polymer framework, with less molecular motion. The tan delta values for the single layer and 7-layer Alg-Az-PEGD beads are quite similar, as can be seen in the three bottom plots in FIG. 6.

Table 2 provides a summary of dynamic mechanical analysis data in the linear region obtained from oscillation tests for the materials described in Table 1.

TABLE 2

| | ITL-A | ITL-B | ITL-C | ITL-D | ITL-D |
|---|---|---|---|---|---|
| E' (kPa) | 21.7 | 7.7 | 2.7 | 2.0 | 2.0 |
| Tan delta | 0.17 | 0.11 | 0.03 | 0.04 | 0.04 |

The values in Table 2 further illustrate the points above. Of the alginate materials evaluated, the APA material, ITL-A, is the least ordered, most ductile, as evidenced by its E' and tan delta values. In contrast, the Alg-Az-PEGD material is the most ordered, least ductile.

The covalently surface crosslinked alginates exhibit surprising mechanical stability, i.e., maintaining their structural integrity and semi-permeability over a prolonged period of time (for at least 90 days) under simulated in vivo conditions (1 mM PBS/37° C.), making them ideally suited for therapeutic and other uses.

Example 8

Synthesis of Biocompatible Polymers Comprising Phosphocholine and Lysine

Illustrative phosphocholine and lysine copolymers were designed and synthesized as described below.

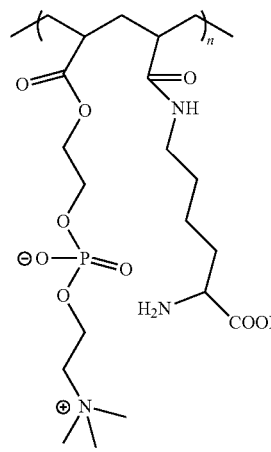

PC monomer
Phosphocholine methacrylamide

Lysine methacrylamide

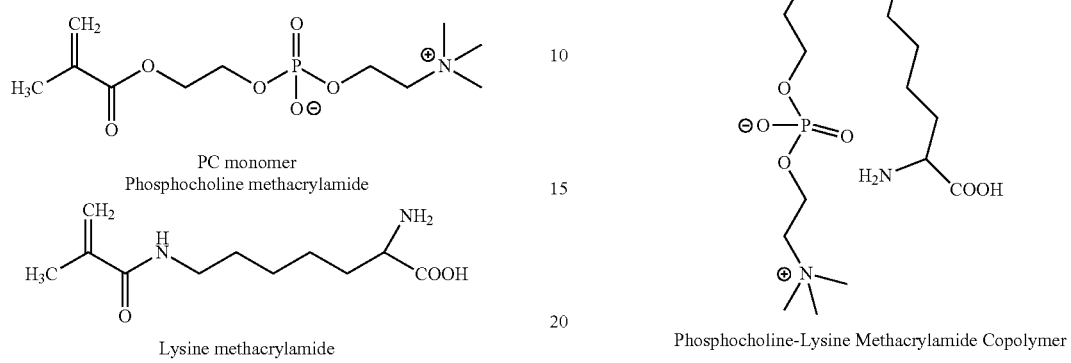

Phosphocholine-Lysine Methacrylamide Copolymer

Scheme 1 Synthesis of water soluble PC-Lysine methacrylamide copolymer bearing click reactive moieties.

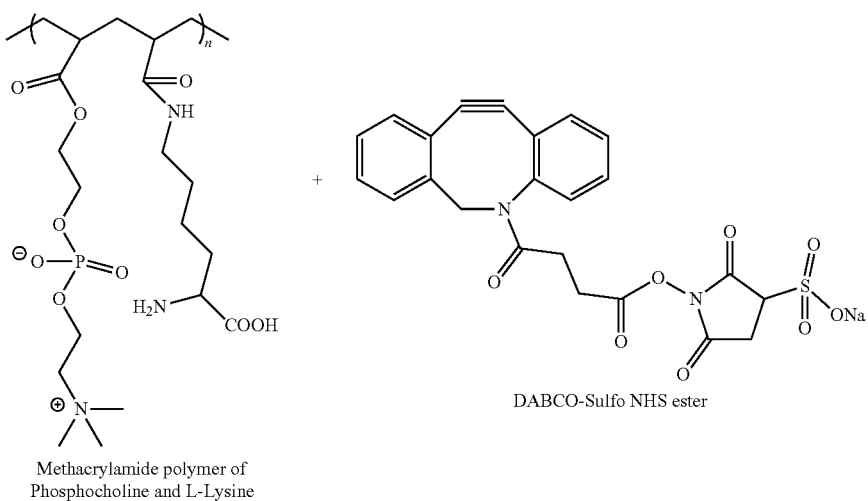

Methacrylamide polymer of Phosphocholine and L-Lysine

DABCO-Sulfo NHS ester

Water, NaHCO₃

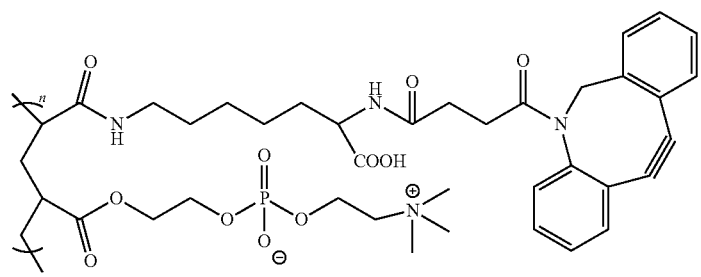

water soluble 'click reactive' coating agent with bio-compatible Phosphocholine groups on polymer surface Scheme 2 Synthesis of water soluble PC-Lysine methacrylamide copolymer bearing exemplary click reactive moieties and having short PEG linker

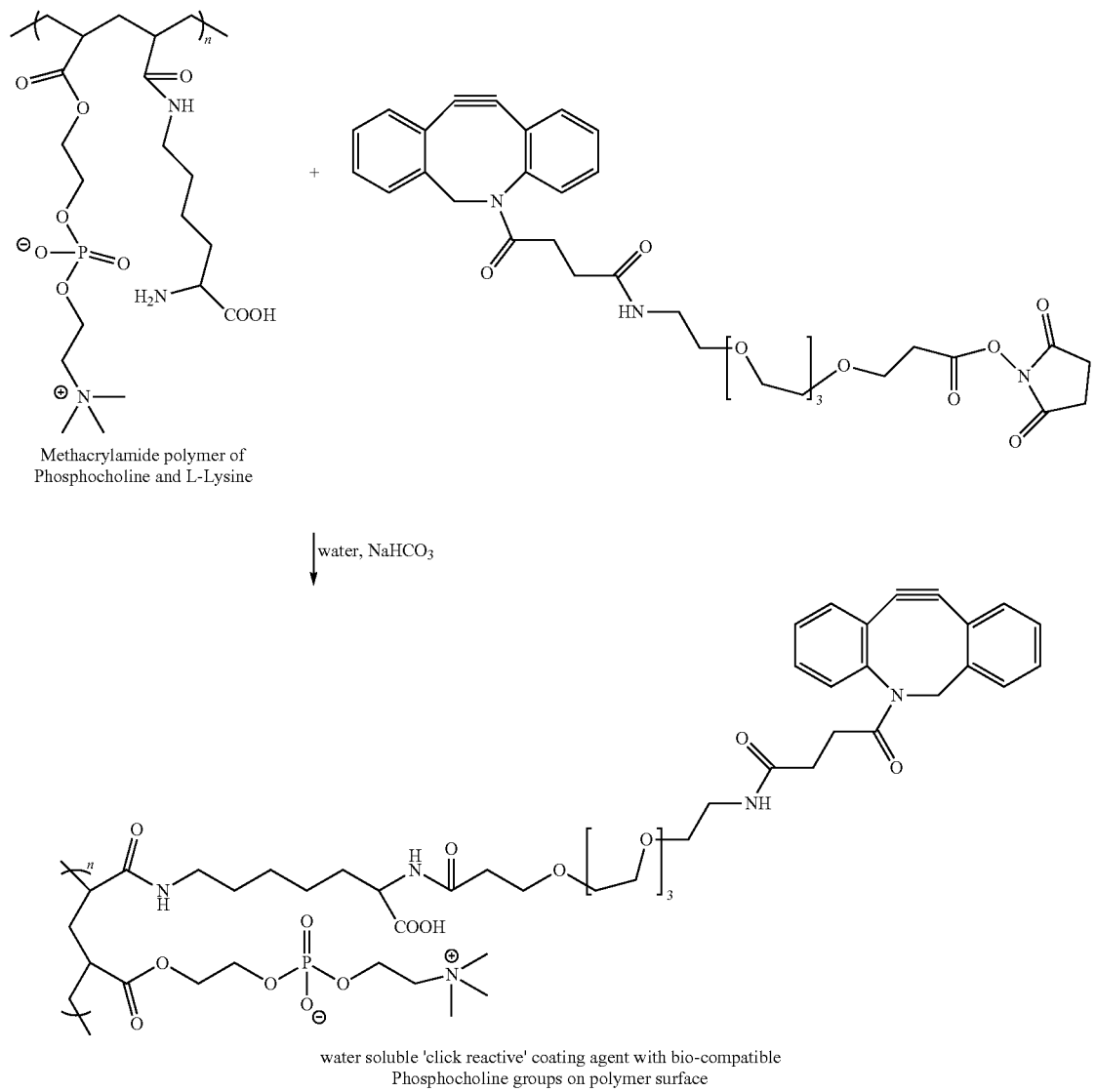

water soluble 'click reactive' coating agent with bio-compatible Phosphocholine groups on polymer surface 8A. Synthesis of Methacrylamide Copolymer of Phosphocholine (PC) and Lysine (10 Mole % Lysine) "PC-Lys-MA Copolymer")

A 50 ml two neck round bottom flask was charged with 2-methacryloxy phosphocholine (1.18 g, 4 mmol) and N-methacryloyl L-lysine (85 mg, 0.4 mmol) and a stir bar. Nitrogen gas was purged with a needle for 10 minutes prior to the addition of de-ionized water (10 ml); the resulting mixture was stirred until a clear solution was formed. Nitrogen gas was continuously purged throughout the reaction. To the reaction mixture was added a water soluble azo-initiator, 2,2'-azobis(2-methylpropionamidine)dihydrochloride (V-50). The initiator was dissolved within 2 to 3 minutes after the addition. The flask was heated to 60° C. and maintained under controlled temperature conditions for 16 hours under a nitrogen atmosphere. The resultant viscous solution was allowed to cool to room temperature. The viscous solution was poured into isopropanol (200 ml). The polymer was precipitated as white mass. The solvent was decanted and dried to remove the solvent under vacuum. The polymer was dissolved in water (30 ml), and the viscous solution was poured dropwise into isopropanol. The polymer was collected and dried under vacuum, followed by three additional rounds of dissolution in water followed by precipitation in isopropanol. The polymer was dried under vacuum to give a white powder (1.2 g). The molecular weight of the product (GPC analysis) was ~300 kD.

8B: Synthesis of Methacrylamide Copolymer of Phosphocholine and Lysine (16.6 Mole % Lysine)

A 50 ml two neck round bottom flask was charged with 2-methacryloxy phosphocholine (1.181 g, 4 mmol) and N-methacryloyl L-lysine (170 mg, 0.8 mmol) and a stir bar. The flask was purged with nitrogen gas for 10 minutes prior to the addition of de-ionized water (10 ml); the resulting mixture was stirred until a clear solution was formed. Nitrogen gas was continuously purged throughout the reaction. A water soluble azo-initiator 2,2'-azobis (2-methylpropionamidine) dihydrochloride (V-50) was added to the reaction mixture. The initiator was dissolved within 2 to 3 minutes after the addition. The flask was heated to 60° C.

and maintained at this temperature under controlled conditions for 16 hours under a nitrogen atmosphere. The resulting viscous solution was allowed to cool to room temperature. The viscous solution was poured into isopropanol (200 ml). The polymer was precipitated as white mass. The solvent was decanted and dried to remove the solvent under vacuum. The polymer was dissolved in water (30 ml), and the viscous solution was poured dropwise into isopropanol. The polymer was collected and dried under vacuum, followed by three additional rounds of dissolution in water followed by precipitation in isopropanol. The polymer was collected and dried under vacuum. Again it was dissolved in water and precipitated in iso-propanol. After three times of re-precipitation, finally the polymer was dried under vacuum at to give white powder (1.3 g).

8C.: Coupling of DBCO-Sulfo-NHS Ester to PC-Lys-MA Copolymer:

A methacrylamide copolymer of phosphocholine and lysine (16.6 mole % lysine), as described in Example 8B, (300 mg) was dissolved in 5 ml water, and the pH was adjusted to 7.4 by addition of $NaHCO_3$ powder (~10 mg). To this was added DBCO-sulfo-NHS ester (50 mg, 0.094 mmol)) followed by stirring at room temperature for 3 hours. The pH was maintained at 7.3 by adding $NaHCO_3$ powder (5 mg) within 15 min, and the pH was monitored occasionally. After three hours, the reaction mixture was dialyzed (using a 5K mol wt cut off membrane). The solution was lyophilized. The polymer was obtained as a white flaky material.

8D. Coupling of $DBCO-PEG_4$-NHS Ester to Copolymer:

A methacrylamide copolymer of phosphocholine and lysine, PC-Lys-MA (16.6 mole % lysine; 300 mg) was dissolved in 5 ml water, and the pH was adjusted to 7.4 by adding $NaHCO_3$ powder (~-10 mg). To the above solution was added $DBCO-PEG_4$-NHS ester (50 mg), followed by stirring at room temperature for 3 hours. The pH was maintained at 7.3 by adding $NaHCO_3$ powder (5 mg) within 15 min, followed by occasional monitoring of the pH. After three hours, the reaction mixture was dialyzed (5K mol wt cut off membrane). The solution was lyophilized. The polymer was obtained as white powder.

8E: Gel Formation Testing of DBCO-Coupled Phosphocholine-Lysine Methacrylamide Polymers (DBCO-PC-Lys-MA)

A solution (2%) of the DBCO-PC-Lys-MA polymer described in Example 8C or 8D was prepared by dissolving the copolymer in water at room temperature. A solution (10%) of 4-arm PEG azide was prepared by dissolving 4-arm PEG azide (mol wt 5K) in water at room temperature. A clear glass vial was charged with the DBCO-PC-Lys-MA polymer (100 microliters), followed by addition of the PEG azide solution (100 microliters). The mixture was swirled slightly. Immediately, a transparent gel was obtained. This result indicates that the DBCO-PC-Lys-MA polymer is active, and suitable, e.g., for coating alginic acid beads containing azide groups on the surface as described herein, to provide a final coating with a biocompatible click-reactive polymer.

What is claimed is:

1. A method of preparing a hydrogel composition comprising an alginate matrix covalently crosslinked in its periphery to a multi-armed water soluble polymer, the method comprising:
   (i) reacting an aqueous mixture comprising an alginate matrix having from about 3 mol % to about 50 mol % of its alginate carboxyl groups carrying a second functional group with a multi-armed water soluble polymer comprising a first functional group at a terminus of one or more of its polymer arms at a temperature ranging from about 0° C. to 60° C., wherein the first and second functional groups are selectively chemically reactive under mild reaction conditions to form covalent links to thereby provide the hydrogel composition comprising the alginate matrix covalently crosslinked in its periphery to the multi-armed water soluble polymer, wherein the reacting step is carried out over a period of from 5 minutes to 2 hours;
   wherein the alginate matrix having from about 3 mol % to about 50 mol % of its alginate carboxyl groups carrying a second functional group is "ALG-B"; and wherein the multi-armed water soluble polymer comprising a first functional group at a terminus of one or more of its polymer arms is "POLY-A".

2. The method of claim 1, wherein the aqueous mixture comprises from about 0.5 to 25 weight percent of the alginate matrix.

3. The method of claim 2, wherein the concentration of the multi-armed water soluble polymer in the aqueous mixture ranges from about 0.1 weight percent to about 50 weight percent.

4. The method of claim 1, further comprising separating the hydrogel composition in step (i) from the aqueous mixture.

5. The method of claim 4, further comprising washing the hydrogel composition with an isotonic solution.

6. The method of claim 1, wherein ALG-B comprises divalent or multi-valent cations.

7. The method of claim 1, wherein ALG-B has a weight average molecular weight in a range from about 10,000 to about 300,000 g/mol.

8. The method of claim 1, wherein the multi-armed water soluble polymer has a weight average molecular weight in a range from 1,000 to about 50,000 daltons.

9. The method of claim 1, wherein the multi-armed water soluble polymer is a polyethylene glycol having from 3 to 10 linear polyethylene glycol arms each terminating with a first functional group.

10. The method of claim 9, wherein the first functional group is a dibenzyl cyclooctyne amine and the second functional group is azide.

11. The method of claim 9, wherein the first functional group is norbornene and the second functional group is thiol or tetrazine.

12. The method of claim 1, wherein the molar ratio of the first functional group to the second functional group is greater than one to thereby provide the hydrogel composition comprising unreacted first functional groups in the covalently crosslinked periphery of the alginate matrix.

13. The method of claim 12, further comprising reacting the hydrogel composition with ALG-B in an aqueous mixture at a temperature ranging from about 0° C. to 60° C.

14. The method of claim 13, further comprising sequential additions of POLY-A or ALG-B to the hydrogel composition.

15. The method of claim 1, wherein the ALG-B from step (i) is in the form of a microcapsule, bead, sheet, fiber, membrane, microparticle, sponge, mesh, suture, foam, composite, scaffold or composite of the foregoing.

16. The method of claim 1, wherein the ALG-B from step (i) comprises a pharmacologically active material encapsulated therein.

17. The method of claim 16, wherein the pharmacologically active material is selected from the group consisting of proteins, polynucleotides, and small molecules.

18. The method of claim 1, wherein the ALG-B from step (i) comprises living cells.

19. The method of claim 18, wherein the living cells are autologous cells, allogeneic cells, xenogeneic cells, induced pluripotent stem-derived cells, induced pluripotent stem-derived pancreatic progenitor cells, platelets, T-Cells, CAR-T cells, cardiac myoblasts, genetically modified APRE-19 cells, pancreatic cells, dermal cells, hormone, cytokine, pancreatic, or growth factor secreting cells.

20. The method of claim 12, wherein the molar ratio of the first functional group to the second functional group is in a range of about 1.1 to 5.

* * * * *